(12) United States Patent
Chanot et al.

(10) Patent No.: US 8,569,518 B2
(45) Date of Patent: Oct. 29, 2013

(54) BICYCLIC DIOXANES, THEIR PREPARATION AND THEIR USE AS FRAGRANT COMPOUNDS

(75) Inventors: Jean-Jacques Chanot, Speracedes (FR); Jean Mane, Grasse (FR); Caroline Plessis, Châteauneuf (FR)

(73) Assignee: V. Mane Fils, Bar sur Loup (FR)

( * ) Notice: Subject to any disclaimer, the term of this patent is extended or adjusted under 35 U.S.C. 154(b) by 0 days.

(21) Appl. No.: 13/387,214

(22) PCT Filed: Jul. 28, 2010

(86) PCT No.: PCT/IB2010/053424
§ 371 (c)(1),
(2), (4) Date: Mar. 15, 2012

(87) PCT Pub. No.: WO2011/013077
PCT Pub. Date: Feb. 3, 2011

(65) Prior Publication Data
US 2012/0165557 A1    Jun. 28, 2012

(30) Foreign Application Priority Data
Jul. 29, 2009  (EP) .................................. 09305713

(51) Int. Cl.
*C07D 319/08* (2006.01)

(52) U.S. Cl.
USPC ......................................... 549/336; 549/365

(58) Field of Classification Search
USPC ................................ 549/336, 365
See application file for complete search history.

(56) References Cited

U.S. PATENT DOCUMENTS 6,303,798 B1  10/2001  Belko et al.

FOREIGN PATENT DOCUMENTS

DE        102 25 350        12/2003

OTHER PUBLICATIONS

Sirtwistle et al., Stereoselectivity in the Hydroboration of Chiral Cyclohexane-Derived Allylic Alcohols, 1986, Tetrahedron Letters, vol. 27, No. 36, 4367-4370.*
Kraft et al, "Odds and Trends: Recent Developments in the Chemistry of Odorants", 2000, pp. 2980-3010, vol. 39, Angew. Chem. Int. Ed.
International Search Report for PCT/IB2010/053424, 2010.
Written Opinion of the International Searching Authority for PCT/IB2010/053424, 2010.
D.H. Brown et al: "Stereoselectivity in the hydroboration of chiral cyclohexane-derived allylic alcohols" Tetrahedron Letters, vol. 27, 1986, pp. 4367-4370.
M.P. Sibi and S. Nad: "Enantioselective Radical Reactions: Stereoselective Aldol Synthesis from Cyclic Ketones" Angewandte Chemie International Edition, vol. 46, 2007, pp. 9231-9234.
Anonymous: "Stereochemical analysis"[Online] 2007, p. 12, XP002604471, Angewandt Chemie—Retrieved from the Internet: URL:http://www.wiley-vch.de/contents/jc_20_02/2007/z7029 76_s.pdf>, [retrieved on Sep. 22, 2010].

* cited by examiner

*Primary Examiner* — Kristin Vajda
(74) *Attorney, Agent, or Firm* — B. Aaron Schulman, Esq.; Stites & Harbison PLLC

(57) ABSTRACT

The invention is directed to the use of compounds of formula (I), as fragrant agents. In this formula: —$R^3$ and $R^4$ are independently a hydrogen atom, a C1-C6 alkyl group or a C2-C6 alkenyl group, $R^5$ is a C1-C6 alkyl group, a C2-C6 alkenyl group or a $(CH_2)_{0-2}$-aryl group, $R^6$ is a C1-C6 alkyl group, a C2-C6 alkenyl group, a $(CH2)_{0-2}$-aryl group or a C5-C6 cycloalkyl or cycloalkenyl group, and $R^7$ is a hydrogen atom, a C1-C6 alkyl group or a C2-C6 alkenyl group; or $R^3$, $R^4$ and $R^5$ are as above defined, and $R^6$ and $R^7$ together with the carbon atom to which they are attached form a C5-C6 cycloalkyl or cycloalkenyl group.

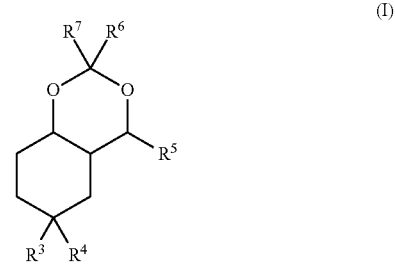

15 Claims, No Drawings

BICYCLIC DIOXANES, THEIR PREPARATION AND THEIR USE AS FRAGRANT COMPOUNDS

FIELD OF THE INVENTION

The invention relates to the field of fragrances. More particularly, the invention relates to bicyclic dioxanes, their method of preparation, and their use in the fields of perfumery.

BACKGROUND

Acetals form an important class of compounds in the field of aromatic chemistry, especially for use in basic media. The most important acetals are cyclic and are known for their fruity, floral or ambery fragrance (Kraft, P., Bajgrowicz, J. A., Angew. Chem. Int. Ed. 2000, 39, 2980-3010).

In the fruity notes, examples of commercially available acetals comprise Methyl Pamplemousse® (1), Floropal® (2), and Oxane® (3). These compounds are widely used in the field of perfumery. In the floral notes, rosy notes are quite important. One example of a cyclic dioxane having a floral note is Magnolan®. It is interestingly used to bring freshness, in particular to lily of the valley accords. Examples of cyclic dioxanes having ambery notes include Okoumal (6), Karanal (5), and Spirambrene (7). Okoumal possesses a powerful ambery fragrance which blends very well to woody accords. Karanal and Spirambrene also have a tenacious odour.

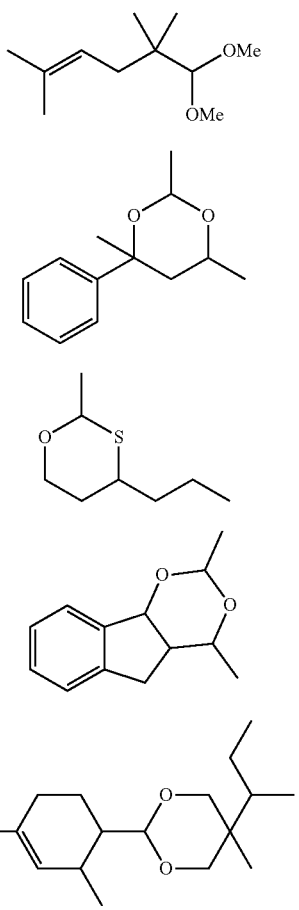

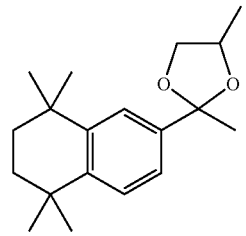

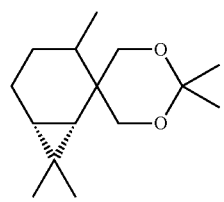

PROBLEM TO BE SOLVED

The need for new compounds is of great importance for the development of the fragrance industry, which recently had to face stricter international regulatory requirements about the use of certain materials, as well as environmental concerns and customer demands for improved performance. Moreover, a phenomenon that is more and more frequently observed in the fields of perfumery are allergies to fragrant compounds. One way of minimizing the risk of allergies is regularly replacing fragrant compounds in perfumes. There is thus a constant need for new fragrant compounds that may be used to replace existing ones due to their similar fragrance.

Providing new fragrant compounds as well as means of selectively manufacturing such compounds is therefore an object of the invention.

The Applicant thus focused on the synthesis of new bicyclic acetals, more precisely bicyclic 1,3-dioxanes. Surprisingly and unexpectedly, the new 1,3-dioxane derivatives did not present the expected ambery notes, but mainly unexpected green notes.

SUMMARY OF THE INVENTION

The invention is directed to the use of compounds of formula:

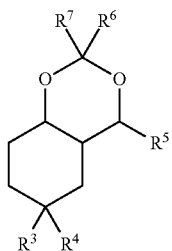

as fragrant agents. In this formula:
R$^3$ and R$^4$ are independently a hydrogen atom, a C1-C6 alkyl group or a C2-C6 alkenyl group,
R$^5$ is a C1-C6 alkyl group, a C2-C6 alkenyl group or a (CH$_2$)$_{0-2}$-aryl group, $R^6$ is a C1-C6 alkyl group, a C2-C6 alkenyl group, a $(CH_2)_{0-2}$-aryl group or a C5-C6 cycloalkyl or cycloalkenyl group, and $R^7$ is a hydrogen atom, a C1-C6 alkyl group or a C2-C6 alkenyl group;

or $R^3$, $R^4$ and $R^5$ are as above defined, and $R^6$ and $R^7$ together with the carbon atom to which they are attached form a C5-C6 cycloalkyl or cycloalkenyl group.

Among the compounds defined by the formula (I) and used according to the invention as fragrant agents, to the inventors' knowledge, some are novel. In this context, the invention is also directed to compounds of formula (I), as defined above, with the proviso that said compound are not:
2,2-dimethyl-4-ethylhexahydrobenzo[1,3]dioxine
2,2-dimethyl-4-n-penthylhexahydrobenzo[1,3]dioxine
2,2-dimethyl-4-phenylhexahydrobenzo[1,3]dioxine
2,4-dimethylhexahydrobenzo[1,3]dioxine
2,4-diphenylhexahydrobenzo[1,3]dioxine
4-ethyl-2-methylhexahydrobenzo[1,3]dioxine
4-methyl-2-phenylhexahydrobenzo[1,3]dioxine
2,2,4-trimethylhexahydrobenzo[1,3]dioxine.

This invention relates to the compounds of formula (I), as described above, as well as to any of their various stereoisomers.

The invention is also directed to a method of preparation of compounds of formula (I) as defined above.

DETAILED DESCRIPTION OF THE INVENTION

As set forth above, the invention is directed to compounds of formula:

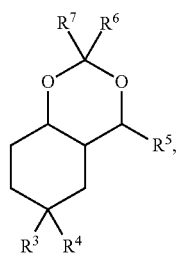

(I)

as previously defined, and to the use of this type of compounds as fragrant agents.

Preferably, $R^3$ and $R^4$ are independently selected from the group consisting of a hydrogen atom, methyl, ethyl, i-propyl, i-butyl, and t-butyl, more preferably from the group consisting of a hydrogen atom, methyl and t-butyl.

$R^5$ is preferably selected from the group consisting of methyl, ethyl, i-propyl, i-butyl, t-butyl, n-pentyl, 1-propen-1-yl, allyl, vinyl, and phenyl, more preferably from the group consisting of methyl, ethyl, i-butyl and phenyl.

$R^6$ is preferably selected from the group consisting of methyl, ethyl, n-propyl, i-propyl, n-butyl, i-butyl, t-butyl, n-pentyl, 1-propen-1-yl, phenyl, benzyl and 2,4-dimethylcyclohexen-3-yl, more preferably from the group consisting of methyl, ethyl, i-propyl, n-pentyl, 1-propen-1-yl, phenyl, benzyl and 2,4-dimethylcyclohexen-3-yl. $R^7$ is then preferably selected from the group consisting of a hydrogen atom, methyl, ethyl, n-propyl, i-propyl, n-butyl, i-butyl, t-butyl, n-pentyl and 1-propen-1-yl, more preferably from the group consisting of hydrogen atom, methyl and n-butyl.

Alternatively, $R^6$ and $R^7$, together with the carbon atom to which they are attached form a cyclopentyl or cyclohexyl group, preferably a cyclopentyl group.

According to a first preferred embodiment, $R^3$ and $R^4$ are hydrogen atoms. In this first embodiment, advantageously:

$R^5$ is selected from the group consisting of methyl, ethyl, i-butyl and phenyl, and more preferably methyl, $R^6$ is selected from the group consisting of methyl, ethyl, i-propyl, phenyl, benzyl and 2,4-dimethylcyclohexen-3-yl, and more preferably ethyl or benzyl, $R^7$ is selected from the group consisting of a hydrogen atom, methyl and n-butyl, and more preferably a hydrogen atom.

According to a second preferred embodiment, $R^3$ and $R^7$ are hydrogen atoms, and $R^4$ is t-butyl. In this second embodiment, advantageously:

$R^5$ is methyl, ethyl or phenyl, and $R^6$ is methyl or i-propyl.

In a third preferred embodiment, $R^3$ and $R^4$ are methyls, and $R^7$ is a hydrogen atom. In this third embodiment, advantageously:

$R^5$ is methyl or ethyl, and $R^6$ is selected from the group consisting of methyl, i-propyl and 1-propen-1-yl.

Particular preferred compounds of formula (I) are those of table hereafter:

| | $R_3$ | $R_4$ | $R_5$ | $R_6$ | $R_7$ | Olfactive profile |
|---|---|---|---|---|---|---|
| Iaa | H | H | Me | Me | H | green, earthy, roasted nuts, coffee |
| Iab | H | H | Me | n-$C_5H_{11}$ | H | green, fatty |
| Iac | H | H | Me | ⤳⟶ | H | green, ripe fruit |
| Iad | H | H | Me | Ph | H | green |
| Iae | H | H | Me | Bz | H | floral (mimosa, carnation), spicy (eugenol), honey |
| Iaf | H | H | Me | Et | H | powerful, spicy (curry, eugenol), hazelnut, fenugrec, coffee beans, celery, tagete, immortelle, fruity (pear, apple, carrot) |
| Iah | H | H | Me | Me | Me | green, minty, fresh |
| Iai | H | H | Me | Me | n-Bu | camphoraceous, pharmaceuticals, caoutchouc |
| Iaj | H | H | Me | —$(CH_2)_4$— | | peanut, animal, clean |
| Iak | H | H | Me | cyclohexenyl | H | green, floral, a bit animalic |
| Ial | H | H | Me | —[CH=CH—$(CH_2)_3$]— | | herbaceous, earthy, spicy |
| Ibg | H | H | Et | i-Pr | H | herbaceous, camomile |
| Ica | H | H | Ph | Me | H | spicy, exotic fruits |
| Ida | H | H | i-Bu | Me | H | leathery, cresol |
| I'aa | H | t-Bu | Me | Me | H | sulfur, fatty |

-continued

| | $R_3$ | $R_4$ | $R_5$ | $R_6$ | $R_7$ | Olfactive profile |
|---|---|---|---|---|---|---|
| I'bg | H | t-Bu | Et | i-Pr | H | herbaceous, camomile, woody |
| I'ca | H | t-Bu | Ph | Me | H | green, chemicals |
| I"aa | Me | Me | Me | Me | H | aromatic, woody, powerful. |
| I"ac | Me | Me | Me | ⌇⏥⏥ | H | herbal, minty, fruity |
| I"bg | Me | Me | Et | i-Pr | H | herbaceous |

The compounds of formula (I) as defined above exhibit interesting olfactive properties. Very unexpectedly and surprisingly, they do not show the typical floral, ambery or fruity notes that the skilled person would have expected, but rather green and/or spicy notes.

In another aspect, the invention therefore relates to the use of the compounds of formula (I) as described above as fragrant agents. This invention also relates to a fragrant composition containing at least one compound of formula (I) according to the invention.

This invention includes any fragrant composition comprising, as a fragrant or flavouring agent, at least a compound of formula (I). The compounds of the invention may be used alone or in combination with other perfuming ingredients, solvents, additives or fixatives, commonly used and that the person skilled in the art is able to choose in regard of the desired effect and the nature of the product to perfume.

In a first embodiment, the invention relates to the use of a compound of formula (I) according to the invention or a composition containing at least one of such a compound in the perfumery field for the preparation of perfumed bases and concentrates, fragrances, perfumes and similar products (e.g. topic compositions, cosmetic compositions such as for example face and body creams, cleansers, facial treatments, talc powders, hair oils, shampoos, hair lotions, bath oils and salts, shower and bath gels, soaps, body anti-perspirants and deodorizers, pre-shave, shaving and post-shave creams and lotions, creams, toothpastes, mouth baths, pomades, cleaning products, such as for example softeners, detergents, air deodorizers and household cleaning supplies. Therefore, the invention also relates to a fragrant composition including at least one compound of formula (I).

In a second embodiment, the invention relates to the use of the compounds or composition as described above, as masking agents of odours, and to any pharmaceutical or cosmetic composition containing at least one compound of formula (I) or one or more isomers of a compound of formula (I). Therefore, this invention also relates to any composition comprising at least one compound of formula (I), as herein described, in combination with any suitable excipient, especially pharmaceutical or cosmetic excipient.

In another aspect, the invention also relates to a method of fragrancing a composition by adding an olfactory effective amount of a compound of formula (I) of the invention to said composition. Suitable compositions comprise perfumed bases and concentrates, fragrances, perfumes and similar products; topic compositions; cosmetic compositions such as for example face and body creams, cleansers, facial treatments, talc powders, hair oils, shampoos, hair lotions, bath oils and salts, shower and bath gels, soaps, body anti-perspirants and deodorizers, pre-shave, shaving and post-shave creams and lotions, creams, toothpastes, mouth baths, pomades; cleaning products, such as for example softeners, detergents, air deodorizers and household cleaning supplies.

In yet another aspect, the invention also relates to a method of masking odours comprising adding an olfactory effective amount of at least a compound of formula (I) of the invention to a composition. Suitable compositions comprise particularly pharmaceutical, and cosmetic compositions. Suitable cosmetic composition include face and body creams, cleansers, facial treatments, talc powders, hair oils, shampoos, hair lotions, bath oils and salts, shower and bath gels, soaps, body anti-perspirants and deodorizers, pre-shave, shaving and post-shave creams and lotions, creams, toothpastes, mouth baths, and pomades.

The compounds of the invention may be used in a concentration comprised in a range from 0.001% to 99% in weight, preferably from 0.1% to 50% in weight, more preferably from 0.1% to 30% in weight. It is known by the man skilled in the art that these values depend of the nature of the composition/article to be perfumed, the desired intensity of the perfume, and of the nature of the other ingredients present in said composition or article.

The invention also relates to a process of preparing a compound according formula (I) as defined above, the process comprising the following steps of:

a) reacting a compound of formula (II) with morpholine so as to obtain an enamine of formula (III)

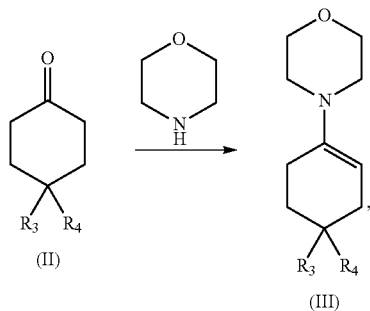

wherein $R^3$ and $R^4$ are as defined above, b) acylating the enamine of formula (III) with $R^5$—COCl, wherein $R^5$ is as defined above, so as to obtain the corresponding acylated enamine

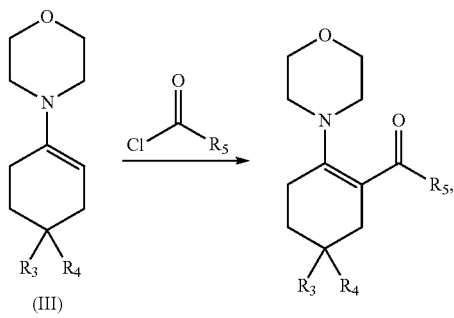

c) hydrolysing the acylated enamine obtained in the previous step in the presence of an acid, such as for example hydrochloric acid so as to obtain a diketone of formula (IV)

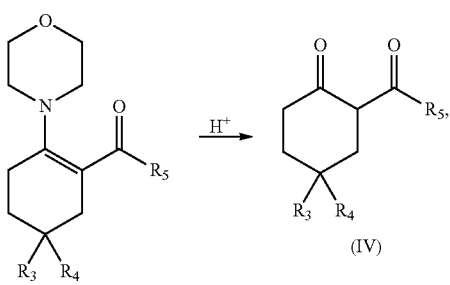

d) reducing the diketone (IV) so as to obtain the corresponding diol (V)

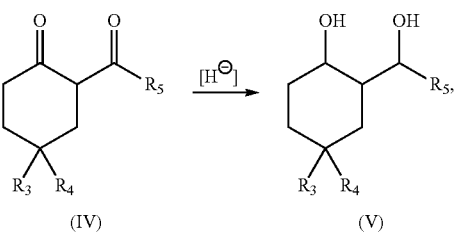

and e) reacting the diol (V) with $R^6$—CO—$R^7$, wherein $R^6$ and $R^7$ are as defined above, so as to obtain the compound of formula (I)

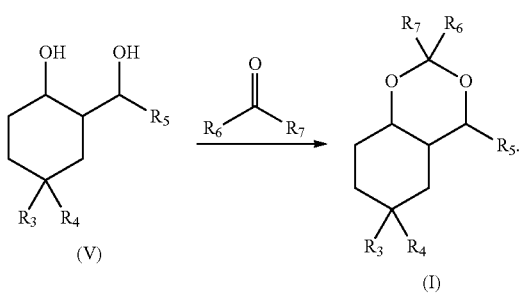

Step a) of the process of the invention is carried out in an organic solvent, which may be selected from the group comprising toluene, xylene, trimethylbenzene, cyclohexane, and methylcyclohexane. According to a preferred embodiment, the organic solvent is cyclohexane or toluene.

The reaction of step a) is advantageously carried out at refluxing temperature.

Step b) is carried out in an organic solvent, which may be selected from the group comprising toluene, xylene, trimethylbenzene, cyclohexane and methylcyclohexane, in the presence of an amine, preferably triethylamine. According to a preferred embodiment, the organic solvent is toluene.

Step c) is advantageously carried out in the same solvent as step b). Preferably, the diketone is directly reacted with the acid without previous purification.

The reduction of the diketone to the diol in step d) is carried out according to conventional reduction methods well known to the person skilled in the art, e.g. using $NaBH_4$, Dibal-H, $LiAlH_4$ or $H_2$. Particularly good results were obtained with $NaBH_4$.

DEFINITIONS

The terms "fragrance" and "fragrant" are used interchangeably whenever a compound or a mixture of compounds is referred to, which is intended to pleasantly stimulate the sense of smell.

The term "olfactory effective amount" means a level or amount of fragrant compound present in a material at which the incorporated compound exhibits a sensory effect.

By the term "masking" is meant reducing or eliminating malodour perception generated by one or more molecules entering in the composition of a product.

The term "isomer" means molecules having the same chemical formula, which means same number and types of atoms, but in which the atoms are arranged differently.

The term "isomer" includes structural isomers, geometric isomers, optical isomers and stereoisomers. It particularly includes the cis/trans isomers, the cis isomers being the ones where the bicyclic junction is cis, i.e. the substituents forming the acetal cycle are on the same side of the cyclohexyl cycle in (I). The trans configuration is the one where the substituents forming the acetal cycle are on two different sides of the cyclohexyl cycle in (I)—the bicyclic junction is trans.

The term "C1-C6 alkyl" or "C1-C6 alkyl group", means any linear or branched saturated hydrocarbon chain having 1, 2, 3, 4, 5 or 6 carbon atoms, such as for example methyl, ethyl, n-propyl, i-propyl, n-butyl, sec-butyl, iso-butyl, tert-butyl, and n-pentyl.

The term "C2-C6 alkenyl" or "C2-C6 alkenyl group", means any linear or branched mono or poly unsaturated hydrocarbon chain, having 2, 3, 4, 5 or 6 carbon atoms, such as for example ethenyl, prop-1-enyl, allyl, but-1-enyl, but-2-enyl or pentenyl.

The term "C5-C6 cycloalkyl" or "C5-C6 cycloalkyl group", means any cyclic saturated hydrocarbon chain having 5 or 6 carbon atoms (namely, a cyclopentyl or cyclohexyl), substituted or not by one or several alkyl and/or alkenyl groups as described above—preferably methyl and ethyl—.

The term "C5-C6 cycloalkenyl" or "C5-C6 cycloalkenyl group", means any cyclic mono or poly unsaturated hydrocarbon chain having preferably 5, 6 or 7 carbon atoms, such as for example cyclopentenyl, cyclohexenyl and cycloheptenyl, substituted or not by one or several alkyl and/or alkenyl groups as described above—preferably methyl and ethyl—.

The term "aryl" refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. A preferred aryl group is phenyl. The term "$(CH_2)_{0-2}$-aryl" thus includes any aryl group as defined above as well as any —$CH_2$-aryl group and any —$(CH_2)_2$-aryl group, wherein the aryl moiety is as defined above. A preferred —$CH_2$-aryl group is the benzyl group and a preferred —$(CH_2)_2$-aryl group is —$(CH_2)_2$-phenyl.

The invention will be better understood with reference to the following examples. These examples are intended to be representative of specific embodiments of the invention, and are not intended as limiting the scope of the invention.

EXAMPLES

Example 1

Preparation of 4-cyclohex-1-enyl-morpholine (III)

Cyclohexanone (98.14 g, 1.00 mol) is added dropwise to a 12M solution of morpholine (118.48 g, 1.36 mol) in cyclohexane (120 ml) at 65-70° C. The reaction mixture is then heated under reflux and the completion of the reaction is followed by GC. The formed water is removed using a Dean-Stark apparatus.

After cooling down, the solvent is removed under vacuum and the crude 4-cyclohex-1-enyl-morpholine (orange liquid, quantitative yield) is used directly in the following step.

Example 2

Preparation of 4-(4-tert-butyl-cyclohex-1-enyl)-morpholine (III')

Compound III' (white solid) is obtained quantitatively according to Example 1, from 4-tert-butylcyclohexanone (77.12 g, 0.50 mol), morpholine (54.01 g, 0.62 mol) and cyclohexane (60 mL).

Example 3

Preparation of 4-(4,4-dimethyl-cyclohex-1-enyl)-morpholine (III")

Compound III" (brown liquid) is obtained quantitatively according to Example 1, from 4,4-dimethylcyclohexanone (350.03 g, 2.76 mol), morpholine (327.01 g, 3.75 mol) and cyclohexane (330 mL).

Example 4

Preparation of 2-acetyl-cyclohexanone (IVa)

To a 0.65 M solution of 4-cyclohex-1-enyl-morpholine (82.64 g, 0.50 mol, 1 eq.), obtained in Example 1, in toluene (770 ml) is added triethylamine (71.33 g, 0.70 mol, 1.41 eq). Acetyl chloride (55.34 g, 0.70 mol, 1.41 eq)) is then added dropwise and the reaction mixture is further stirred at 35° C. for 20 hours and then at room temperature overnight.

After completion of the reaction (followed by GC), a 20% HCl aqueous solution (250 mL) is added and the mixture is stirred under reflux for 1 hour.

After cooling down, the organic phase is washed twice with water, once with saturated aqueous $NaHCO_3$ solution and with brine. The organic phase is then dried over magnesium sulphate and the solvents are evaporated. The crude oil is then purified by distillation to give compound IVa as a colourless oil (49.95 g, 0.36 mol, 72% yield).
Bp: 48° C./0.6 torr Example 5

Preparation of 2-propionyl-cyclohexanone (IVb)

Compound IVb is obtained in 49% yield as a colourless oil, according to Example 4, from 4-cyclohex-1-enyl-morpholine (82.64 g, 0.50 mol, obtained in Example 1), triethylamine (71.33 g, 1.41 mol), propionyl chloride (64.76 g, 1.41 mol), toluene (770 mL) and 20% aqueous HCl (250 mL).
Bp: 98° C./5.4 torr Example 6

Preparation of 2-benzoyl-cyclohexanone (IVc)

Compound IVc is obtained in 50% yield as a yellow powder, according to Example 4, from 4-cyclohex-1-enyl-morpholine (40.96 g, 0.25 mol, obtained in Example 1), triethylamine (35.35 g, 0.35 mol), benzoyl chloride (49.19 g, 0.35 mol), toluene (380 mL) and 20% aqueous HCl (125 mL).
Bp: 110° C./0.3 torr Example 7

Preparation of 2-(3-methylbutanoyl)cyclohexanone (IVd)

Compound IVd is obtained in 90% yield as a pale yellow liquid, according to Example 4, from 4-cyclohex-1-enyl-morpholine (82.64 g, 0.5 mol, obtained in Example 1), triethylamine (71.34 g, 0.71 mol), isovaleryl chloride (85.01 g, 0.71 mol), toluene (760 mL) and 20% aqueous HCl (166 mL).
Bp: 76° C./0.68 torr Example 8

Preparation of 2-acetyl-4-tert-butyl-cyclohexanone (IV'a)

Compound IV'a is obtained in 53% yield as a yellow oil, according to Example 4, from morpholino-enamine III' (36.89 g, 0.17 mol, obtained in Example 2), triethylamine (24.25 g, 0.24 mol), acetyl chloride (18.84 g, 0.24 mol), toluene (260 mL) and 20% aqueous HCl (85 mL).
Bp: 74° C./0.5 torr Example 9

Preparation of 4-tert-butyl-2-propionyl-cyclohexanone (IV'b)

Compound IV'b is obtained in 58% yield as a yellow oil, according to Example 4, from morpholino-enamine III' (36.89 g, 0.17 mol, obtained in Example 2), triethylamine (24.25 g, 0.24 mol), propionyl chloride (22.2 g, 0.24 mol), toluene (260 mL) and 20% aqueous HCl (85 mL).
Bp: 98° C./0.7 torr Example 10

Preparation of 2-benzoyl-4-tert-butyl-cyclohexanone (IV'c)

Compound IV'c is obtained in 35% yield as a yellow powder, according to Example 4, from morpholino-enamine III' (36.89 g, 0.17 mol, obtained in Example 2), triethylamine (24.25 g, 0.24 mol), benzoyl chloride (33.73 g, 0.24 mol), toluene (260 mL) and 20% aqueous HCl (85 mL).
Bp: 110° C./0.2 torr Example 11

Preparation of 2-((E)-but-2-enoyl)-4-tert-butyl-cyclohexanone (IV'e)

Compound IV'e is obtained as white crystals, according to Example 4, from morpholino-enamine III' (55.33 g, 0.25 mol, obtained in Example 2), triethylamine (35.66 g, 0.35 mol), crotonyl chloride (36.85 g, 0.35 mol), toluene (380 mL) and 20% aqueous HCl (125 mL).
Bp: 115° C./0.76 torr
Mp: 73.6° C.

Example 12

Preparation of 2-acetyl-4,4-dimethyl-cyclohexanone (IV''a)

Compound IV''a is obtained in 33% yield as a pale yellow oil, according to Example 4, from morpholino-enamine III'' (266.36 g, 1.36 mol, obtained in Example 3), triethylamine (194.04 g, 1.91 mol), acetyl chloride (149.93 g, 1.91 mol), toluene (2.09 L) and 20% aqueous HCl (685 mL).
Bp: 98° C./6.1 torr

Example 13

Preparation of 4,4-dimethyl-2-propionyl-cyclohexanone (IV'''b)

Compound IV'''b is obtained in 26% yield as a orange oil, according to Example 4, from morpholino-enamine III'' (131.88 g, 0.67 mol, obtained in Example 3), triethylamine (95.59 g, 0.94 mol), propionyl chloride (86.96 g, 0.94 mol), toluene (1.03 L) and 20% aqueous HCl (340 mL).
Bp: 64° C./1.1 torr

Example 14

Preparation of 2-(1-hydroxy-ethyl)-cyclohexanol (Va)

Diketone IVa (49.95 g, 0.36 mol, 1 eq., obtained in Example 4) is added dropwise to a 10-15° C. molar suspension of $NaBH_4$ (13.47 g, 0.36 mol, 1 eq.) in EtOH (360 ml). After completion of the reaction (followed by tlc), acetone (65 ml) is added to the reaction mixture. Half of the solvents is then evaporated and the mixture is diluted in water and MTBE. 10% aqueous HCl is added and the aqueous phase is extracted three times with MTBE. The combined organic phases are then washed with saturated aqueous $NaHCO_3$ and with brine. After drying over magnesium sulphate, the organic phase is filtered and the solvents are evaporated to give crude diol Va as a pale yellow oil in quantitative yield. Compound Va is used in the next step without further purification.

Example 15

Preparation of 2-(1-hydroxy-propyl)-cyclohexanol (Vb)

Compound Vb is obtained in 93% yield as a yellow oil, according to Example 4 from diketone IVb (37.73 g, 0.24 mol, obtained in Example 5), $NaBH_4$ (9.14 g, 0.24 mol), ethanol (240 mL) and acetone (40 mL).

Example 16

Preparation of 2-(hydroxy-phenyl-methyl)-cyclohexanol (Vc)

Compound Vc is obtained in quantitative yield as a pale yellow oil, according to Example 14, from diketone IVc (25.03 g, 0.12 mol, obtained in Example 6), $NaBH_4$ (4.67 g, 0.12 mol), ethanol (120 mL) and acetone (20 mL).

Example 17

Preparation of 2-(1-hydroxy-3-methylbutyl)cyclohexanol (Vd)

Compound Vd is obtained in quantitative yield as a colourless oil, according to Example 14, from diketone IVd (46.02 g, 0.25 mol, obtained in Example 7), $NaBH_4$ (9.45 g, 0.25 mol), ethanol (240 mL) and acetone (45 mL).

Example 18

Preparation of 4-tert-butyl-2-(1-hydroxy-ethyl)-cyclohexanol (V'a)

Compound V'a is obtained in quantitative yield as a yellow oil, according to Example 14, from diketone IV'a (15.5 g, 0.08 mol, obtained in Example 8), $NaBH_4$ (3.02 g, 0.08 mol), ethanol (80 mL) and acetone (15 mL).

Example 19

Preparation of 4-tert-butyl-2-(hydroxy-propyl-methyl)-cyclohexanol (V'b)

Compound V'b is obtained in quantitative yield as a yellow oil, according to Example 14, from diketone IV'b (16.7 g, 0.08 mol, obtained in Example 9), $NaBH_4$ (3.02 g, 0.08 mol), ethanol (80 mL) and acetone (15 mL).

Example 20

Preparation of 4-tert-butyl-2-(hydroxy-phenyl-methyl)-cyclohexanol (V'c)

Compound V'c is obtained in 78% yield as a white powder, according to Example 14, from diketone IV'c (14.56 g, 0.06 mol, obtained in Example 10), $NaBH_4$ (2.27 g, 0.06 mol), ethanol (60 mL) and acetone (10 mL).

Example 21

Preparation of 2-(1-hydroxy-ethyl)-4,4-dimethyl-cyclohexanol (V''a)

Compound V''a is obtained in quantitative yield as a pale yellow oil, according to Example 14, from diketone IV''a (72.17 g, 0.43 mol, obtained in Example 12), $NaBH_4$ (16.25 g, 0.43 mol), ethanol (430 mL) and acetone (85 mL).

Example 22

Preparation of 2-(1-hydroxy-propyl)-4,4-dimethyl-cyclohexanol (V''b)

Compound V''b is obtained in quantitative yield as a pale yellow oil, according to Example 14, from diketone IV'''b (29.99 g, 0.16 mol, obtained in Example 13), $NaBH_4$ (6.05 g, 0.16 mol), ethanol (160 mL) and acetone (30 mL).

Example 23

Preparation of 2,4-dimethyl-hexahydro-benzo[1,3]dioxine (Iaa)

Acetaldehyde (28.81 g, 0.40 mol) is added dropwise to a 2.3M solution of diol Va (28.63 g, 0.20 mol, obtained in Example 14) in refluxing cyclohexane (85 ml). The reaction is catalysed with PTSA. The reaction mixture is refluxed for a further 2 hours and the formed water is removed with a Dean-Stark apparatus.

After completion of the reaction (followed by GC), the reaction mixture is cooled down and poured into a half-saturated aqueous $NaHCO_3$ solution. The aqueous phase is extracted twice with MTBE and the combined organic layers are washed with a saturated aqueous $NaHCO_3$ solution and with brine and then dried over magnesium sulphate. The solvents are evaporated and the crude product is purified by distillation to give compound Iaa as a colourless oil in 25% yield. It consists in a mixture of 5 isomers with 2 major isomers (83%) as cis and trans isomers in a 70:30 ratio.

Bp: 65° C./6.5 torr
Olfactory profile: Green, earthy, roasted nuts, coffee
Major Cis-Isomers:
$^1$H-NMR (200 MHz, $CDCl_3$): δ (ppm) 0.70-1.80 (m, 8H); 1.12 (d, 3H, J=6.5 Hz,); 1.32 (d, 3H, J=5.1 Hz,); 1.88 (m, 1H); 3.76 (m, 2H); 4.72 (q, 1H, J=5.1 Hz).
$^{13}$C-NMR (50 MHz, $CDCl_3$): δ (ppm) 17.8; 19.4; 20.5; 21.2; 25.2; 31.7; 39.1; 75.3; 75.5; 98.7.
MS [e/m (%)]: 169 ($M^+$, 5); 155 (10); 127 (3); 109 (39); 98 (9); 93 (11); 89 (29); 82 (100); 67 (75); 55 (16); 43 (18); 41 (15).
Major Trans-Isomers:
$^1$H-NMR (200 MHz, $CDCl_3$, selected data): δ (ppm) 1.17 (d, 3H, J=6.3 Hz); 1.32 (d, 3H, J=5, 1 Hz); 3.21 (dt, 1H, J=4.0 Hz, J=10.2 Hz); 3.38 (dq, 1H, J=6.3 Hz, J=9.5 Hz); 4.78 (q, 1H, J=5.1 Hz).
$^{13}$C-NMR (50 MHz, $CDCl_3$): δ (ppm) 18.5; 21.2; 24.6; 25.3; 25.8; 31.6; 47.2; 76.9; 80.5; 98.4.
MS [e/m (%)]: 169 ($M^+$, 16); 155 (92); 127 (7); 109 (74); 98 (12); 93 (15); 89 (17); 82 (100); 67 (96); 55 (26); 43 (27); 41 (21).
Minor Cis-Isomers:
$^1$H-NMR (200 MHz, $CDCl_3$, selected data): δ (ppm) 5.00 (q, 1H, J=5.0 Hz).
$^{13}$C-NMR (50 MHz, $CDCl_3$, selected data): δ (ppm) 91.4.
MS [e/m (%)]: idem major cis-isomers.

Example 24

Preparation of 4-methyl-2-pentyl-hexahydro-benzo[1,3]dioxine (Iab)

Compound Iab is obtained as a colourless oil in 20% yield, according to Example 23, from diol Va (28.63 g, 0.2 mol, obtained in Example 14), hexanal (24.03 g, 0.24 mol) and cyclohexane (85 ml). It consists in a mixture of 3 isomers with 2 major isomers (98%) in a 50:50 ratio.

Bp: 80° C./0.6 torr
Olfactory profile: green, fatty
$1^{st}$ Isomers:
$^1$H-NMR (200 MHz, $CDCl_3$): δ (ppm) 0.87 (t, 3H, J=6.6 Hz); 1.05-1.20 (m, 3H); 1.06-1.81 (m, 16H); 1.91 (m, 1H); 3.75 (m, 2H); 4.56 (t, 1H, J=4.8 Hz).
$^{13}$C-NMR (50 MHz, $CDCl_3$): δ (ppm) 14.1; 17.8; 19.4; 20.5; 22.6; 23.6; 25.2; 31.7; 31.8; 35.1; 39.3; 75.2; 75.5; 101.9.
MS [e/m (%)]: 225 ($M^+$, 8); 155 (64); 145 (8); 127 (4); 109 (100); 83 (20); 82 (59); 67 (46); 55 (20); 43 (13); 41 (15).
$2^{nd}$ Isomers:
$^1$H-NMR (200 MHz, $CDCl_3$, selected data): δ (ppm) 3.20 (dt, 1H, J=4.0 Hz, J=10.3 Hz); 3.37 (dq, 1H, J=6.2 Hz, J=9.5 Hz); 4.60 (t, 1H, J=5.2 Hz).

$^{13}$C-NMR (50 MHz, $CDCl_3$): δ (ppm) 14.0; 18.6; 22.5; 24.0; 24.6; 25.4; 25.9; 31.7; 31.8; 35.1; 39.3; 77.0; 80.6; 101.8.
MS [e/m (%)]: 225 ($M^+$, 13); 155 (100); 145 (3); 127 (5); 109 (64); 83 (15); 82 (36); 67 (35); 55 (18); 43 (11); 41 (13).

Example 25

Preparation of 4-methyl-2-propenyl-hexahydro-benzo[1,3]dioxine (Iac)

Compound Iac is obtained as a colourless oil in 20% yield, according to Example 23, from diol Va (25.96 g, 0.18 mol, obtained in Example 14), crotonaldehyde (15.14 g, 0.21 mol) and cyclohexane (75 ml). It consists in a mixture of 5 isomers with 2 major isomers (85%) as cis and trans isomers in a 62:38 ratio.

Bp: 62° C./0.6 torr
Olfactory profile: green, ripe fruit
Major Cis-Isomers:
$^1$H-NMR (200 MHz, $CDCl_3$): δ (ppm) 0.75-1.85 (m, 8H); 1.16 (d, 3H, J=6.5 Hz); 1.73 (d, 3H, J=6.4 Hz); 1.95 (m, 1H); 3.85 (m, 2H); 4.98 (d, 1H, J=6.0 Hz); 5.61 (m, 1H); 5.90 (dq, 1H, J=0.5 Hz, J=6.4 Hz).
$^{13}$C-NMR (50 MHz, $CDCl_3$): δ (ppm) 17.4; 17.5; 19.0; 20.1; 24.8; 31.4; 38.9; 75.1; 75.3; 101.0; 128.4; 130.5.
MS [e/m (%)]; 195 ($M^+$, 6); 181 (10); 155 (1); 127 (3); 109 (68); 82 (14); 71 (100); 69 (18); 67 (44); 55 (17); 41 (19).
Major Trans-Isomers:
$^1$H-NMR (200 MHz, $CDCl_3$, selected data): δ (ppm) 1.22 (d, 3H, J=6.2 Hz,); 1.74 (d, 3H, J=6.5 Hz); 3.29 (m, 1H); 3.48 (dq, 1H, J=6.2 Hz, J=9.5 Hz); 5.06 (d, 1H, J=5.7 Hz); 5.97 (dq, 1H, J=0.5 Hz, J=6.5 Hz).
$^{13}$C-NMR (50 MHz, $CDCl_3$): δ (ppm) 17.3; 18.3; 24.3; 25.0; 25.6; 31.3; 47.0; 80.2; 80.3; 101.4; 128.1; 130.4.
MS [e/m (%)]: 195 ($M^+$, 13); 181 (59); 155 (4); 127 (2); 109 (50); 82 (18); 71 (100); 69 (25); 67 (48); 55 (25); 41 (23).

Example 26

Preparation of 4-methyl-2-phenyl-hexahydro-benzo[1,3]dioxine (Iad)

Compound Iad is obtained as a pale yellow oil in 44% yield, according to Example 23, from diol Va (14.98 g, 0.1 mol, obtained in 14), benzaldehyde (21.22 g, 0.2 mol) and cyclohexane (50 ml). It consists in a mixture of 5 isomers with 2 major isomers (84%) as cis/trans isomers in a 60:40 ratio.

Bp: 102° C./0.5 torr
Olfactory profile: green
Major Cis-Isomers:
$^1$H-NMR (200 MHz, $CDCl_3$): δ (ppm) 0.82-1.43 (m, 2H); 1.23 (d, 3H, J=6.5 Hz); 1.44-1.95 (m, 6H); 2.03 (m, 1H); 4.02 (m, 2H); 5.57 (s, 1H); 7.37 (m, 3H); 7.55 (m, 2H).
$^{13}$C-NMR (50 MHz, $CDCl_3$): δ (ppm) 17.9; 20.5; 24.6; 25.2; 31.7; 39.2; 75.9; 76.2; 101.7; 126.4; 128.2; 128.7; 139.2.
MS [e/m (%)]: 231 ($M^+$, 80); 155 (2); 109 (43); 107 (100); 105 (36); 81 (20); 79 (23); 77 (23); 67 (32); 51 (5); 39 (6).
Major Trans-Isomers:
$^1$H-NMR (200 MHz, $CDCl_3$, selected data): δ (ppm) 1.30 (d, 3H, J=6.2 Hz); 3.48 (m, 1H); 3.65 (dq, 1H, J=6.2 Hz, J=9.5 Hz); 5.65 (s, 1H).

$^{13}$C-NMR (50 MHz, CDCl$_3$): δ (ppm) 18.6; 19.5; 25.4; 25.9; 31.7; 47.4; 77.6; 81.1; 101.0; 126.2; 128.2; 128.6; 138.8.

MS [e/m (%)]: 231 (M$^+$, 100); 155 (8); 109 (21); 107 (75); 105 (44); 81 (14); 79 (21); 77 (21); 67 (36); 51 (5); 39 (6).
Minor Isomers:
$^1$H-NMR (200 MHz, CDCl$_3$, selected data): δ (ppm) 5.89 (s, 1H).
$^{13}$C-NMR (50 MHz, CDCl$_3$, selected data): δ (ppm) 32.1.
$^1$H-NMR (200 MHz, CDCl$_3$, selected data): δ (ppm) 5.84 (s, 1H).
$^{13}$C-NMR (50 MHz, CDCl$_3$, selected data): δ (ppm) 31.7.
$^1$H-NMR (200 MHz, CDCl$_3$, selected data): δ (ppm) 5.94 (s, 1H).
$^{13}$C-NMR (50 MHz, CDCl$_3$, selected data): δ (ppm) 31.4.

Example 27

Preparation of
2-benzyl-4-methyl-hexahydro-benzo[1,3]dioxine
(Iae)

Compound Iae is obtained as colourless oil in 30% yield, according to Example 23, from diol Va (25.96 g, 0.18 mol, obtained in Example 14), phenylacetaldehyde (25.23 g, 0.21 mol) and cyclohexane (75 ml). It consists in a mixture of 4 isomers with 2 major isomers (93%) as cis/trans isomers in a 75:25 ratio.
Bp: 90° C./0.2 torr
Olfactory profile: Floral (mimosa, carnation), spicy (eugenol), honey.
Major Cis-Isomers:
$^1$H-NMR (200 MHz, CDCl$_3$): δ (ppm) 1.10 (d, 3H, J=6.6 Hz); 1.20-1.83 (m, 8H); 1.88 (m, 1H); 2.91 (d, 2H, J=5.0 Hz); 3.69 (m, 2H); 4.70 (t, 1H, J=5.0 Hz); 7.23 (m, 5H).
$^{13}$C-NMR (50 MHz, CDCl$_3$): δ (ppm) 17.8; 19.4; 20.5; 25.2; 31.7; 39.2; 41.7; 75.3; 75.5; 101.9; 126.1; 127.9; 129.9; 137.2.
MS [e/m (%)]: 245 (M$^+$, 1); 155 (52); 121 (3); 109 (100); 91 (31); 67 (25); 55 (8); 43 (5); 41 (8).
Major Trans-Isomers:
$^1$H-NMR (200 MHz, CDCl$_3$, selected data): δ (ppm) 1.16 (d, 3H, J=6.3 Hz); 2.91 (d, 2H, J=5.0 Hz); 3.16 (dt, 1H, J=4.0 Hz, J=10.3 Hz); 3.34 (dq, 1H, J=6.3 Hz, J=9.5 Hz); 4.74 (t, 1H, J=5.0 Hz).
$^{13}$C-NMR (50 MHz, CDCl$_3$): δ (ppm) 18.6; 24.5; 25.4; 25.9; 31.6; 41.8; 47.6; 77.1; 80.6; 102.0; 126.2; 128.0; 129.7; 137.1.
MS [e/m (%)]: 245 (M$^+$, 4); 155 (83); 121 (2); 109 (100); 91 (33); 67 (28); 55 (12); 43 (9); 41 (11).

Example 28

Preparation of
2-ethyl-4-methylhexahydro-4H-benzo[d][1,3]dioxine
(Iaf)

Compound Iaf is obtained as colourless oil in 60% yield, according to Example 23, from diol Va (25.96 g, 0.18 mol, obtained in Example 14), propionaldehyde (51 g, 0.88 mol) and cyclohexane (450 ml). It consists principally in a mixture of 5 isomers with 3 major isomers (78%) in a 47:31:22 ratio.
Bp: 80-83° C./5.7 torr
Olfactory profile: powerful, spicy (curry, eugenol), hazelnut, fenugrec, coffee beans, celery, tagete, immortelle, fruity (pear, apple, carrot).

1$^{st}$ Major Cis-Isomers:
$^1$H-NMR (200 MHz, CDCl$_3$): δ (ppm) 0.70-1.05 (m, 1H); 0.92 (t, J=7.5 Hz, 3H); 1.05-1.53 (m, 5H); 1.17 (d, J=6.2 Hz, 3H); 1.53-1.73 (m, 3H); 1.73-2.05 (m, 2H); 3.19 (dt, J=10.1, 4.00 Hz, 1H); 3.38 (tt, J=9.5, 5.3 Hz, 1H); 4.54 (t, J=5.2 Hz, 1H).
$^{13}$C-NMR (50 MHz, CDCl$_3$): δ (ppm) 8.62; 18.56; 24.59; 25.38; 25.88; 28.13; 31.66; 47.54; 76.94; 80.49; 102.70.
MS [e/m (%)]: 184 (M+, 1); 183 (10); 155 (63); 109 (82); 93 (11); 83 (14); 82 (79); 81 (17); 79 (13); 67 (100); 59 (19); 57 (27); 55 (37); 54 (21); 53 (13); 43 (21); 41 (34); 39 (18).
2$^{nd}$ Major Trans-Isomers:
$^1$H-NMR (200 MHz, CDCl$_3$, selected data): δ (ppm) 0.93 (t, J=7.61 Hz, 3H); 1.12 (d, J=6.54 Hz, 3H); 3.67-3.85 (m, 2H); 4.51 (t, J=4.65 Hz, 1H).
$^{13}$C-NMR (50 MHz, CDCl$_3$): δ (ppm) 8.19; 17.8; 19.39; 20.53; 26.63; 28.06; 31.76; 39.32; 75.17; 75.41; 102.50.
MS [e/m (%)]: 184 (M+, <1); 183 (4); 155 (29); 109 (80); 103 (14); 93 (11); 83 (14); 82 (100); 81 (14); 79 (13); 67 (100); 59 (17); 57 (20); 55 (29); 54 (20); 43 (19); 41 (30); 39 (15).
3$^{rd}$ Major Trans-Isomers:
$^1$H-NMR (200 MHz, CDCl$_3$, selected data): δ (ppm) 0.90 (t, J=7.64 Hz, 3H); 1.23 (d, J=6.96 Hz, 3H); 3.45-3.57 (m, 1H); 4.0-4.15 (m, 1H); 4.78 (t, J=5.01 Hz, 1H).
$^{13}$C-NMR (50 MHz, CDCl$_3$): δ (ppm) 8.45; 13.08; 25.23; 25.67; 28.23; 32.14; 43.89; 71.67; 74.18, 95.27.
MS [e/m (%)]: 184 (M+, 1); 183 (9); 155 (66); 127 (10); 109 (100); 93 (13); 83 (12); 82 (40); 81 (15); 79 (11); 67 (90); 59 (15); 57 (33); 55 (37); 54 (17); 53 (12); 43 (19); 41 (32); 39 (17).
1$^{st}$ Minor Isomers:
$^1$H-NMR (200 MHz, CDCl$_3$, selected data): δ (ppm) 1.32 (d, J=7.0 Hz, 3H).
$^{13}$C-NMR (50 MHz, CDCl$_3$, selected data): δ (ppm) 7.99; 16.18; 20.32; 24.59; 25.62; 28.23; 31.58; 38.94; 69.14; 73.86; 95.07.
MS [e/m (%)]: 184 (M+, <1); 183 (4); 155 (40); 109 (100); 93 (11); 83 (10); 82 (30); 81 (11); 79 (9); 67 (70); 59 (10); 57 (19); 55 (26); 54 (11); 43 (14); 41 (23); 39 (11).
2$^{nd}$ Minor Isomers:
$^{13}$C-NMR (50 MHz, CDCl$_3$, selected data): δ (ppm) 44.2; 74.9; 79.6; 97.6.
MS [e/m (%)]: 184 (M+, <1); 183 (2); 155 (40); 109 (100); 93 (5); 83 (10); 82 (38); 81 (12); 79 (10); 67 (73); 59 (17); 57 (21); 55 (29); 54 (15); 43 (16); 41 (26); 39 (13).

Example 29

Preparation of
2,2,4-trimethylhexahydro-4H-benzo[d][1,3]dioxine
(Iah)

Compound Iah is obtained as colourless oil in 14% yield, according to Example 23, from diol Va (40.57 g, 0.28 mol, obtained in Example 14), acetone (32.52 g, 0.56 mol) and cyclohexane (110 ml). It consists in a mixture of 4 isomers with 2 major isomers (96%) as cis/trans enantiomers in a 53:47 ratio.
Bp: 44° C./0.6 torr
Olfactory profile: green, minty, fresh.
Major Cis-Isomers:
$^1$H-NMR (200 MHz, CDCl$_3$): δ (ppm) 0.70-1.30 (m, 4H), 1.06 (d, J=6.46 Hz, 3H), 1.30-1.65 (m, 21-1), 1.40 (s, 3H), 1.41 (s, 3H), 3.45 (dt, J=9.8 Hz, J=3.6 Hz, 1H), 1.65-1.90 (m, 3H), 3.63 (qd, J=9.64 Hz, J=6.09 Hz, 1H).
$^{13}$C-NMR (50 MHz, CDCl$_3$): δ (ppm) 18.14, 19.63, 20.18, 25.14, 25.44, 30.06, 31.75, 39.33, 37.97, 68.17, 98.31.

MS [e/m (%)]: 184 (M+, <1); 169 (54); 127 (11); 109 (100); 93 (6); 82 (18); 81 (11); 67 (68); 59 (77); 55 (23); 54 (11); 43 (62); 41 (25); 39 (14).

Major Trans-Isomers:
$^1$H-NMR (200 MHz, CDCl$_3$, selected data): δ (ppm) 1.11 (d, J=6.09 Hz, 3H), 1.38 (s, 311), 1.45 (s, 3H), 3.90-4.09 (m, 2H).

$^{13}$C-NMR (50 MHz, CDCl$_3$): δ (ppm) 18.41, 19.02, 19.95, 24.64, 25.80, 30.29, 32.12, 47.76, 69.85, 73.14, 98.29.

MS [e/m (%)]: 184 (M+, <1); 169 (100); 127 (19); 109 (94); 93 (10); 82 (26); 81 (15); 67 (83); 59 (95); 55 (35); 54 (15); 43 (89); 41 (34); 39 (21).

Example 30

Preparation of 2-butyl-2,4-dimethylhexahydro-4H-benzo[d][1,3]dioxine (Iai)

Compound Iai is obtained as colourless oil in 10% yield, according to Example 23, from diol Va (40.57 g, 0.28 mol, obtained in Example 14), 2-hexanone (33.65 g, 0.34 mol) and cyclohexane (110 ml). It consists in a mixture of 2 isomers (94%) as cis and trans enantiomers in a 56:44 ratio.

Bp: 60° C./0.47 torr

Olfactory profile: Camphoraceous, pharmaceuticals, caoutchouc.

Major Cis-Isomers:
$^1$H-NMR (200 MHz, CDCl$_3$): δ (ppm) 0.80-0.95 (m, 3H); 1.02-1.20 (m, 5H); 1.20-1.50 (m, 10H); 1.50-1.87 (m, 6H); 3.92-4.13 (m, 2H).

$^{13}$C-NMR (50 MHz, CDCl$_3$, selected data): δ (ppm) 39.07 & 39.38; 67.45 & 67.63; 67.71 & 67.93; 99.35 & 99.41.

MS [e/m (%)]: 226 (M+, <1); 211 (29); 169 (29); 127 (7); 109 (100); 101 (30); 85 (17); 67 (42); 57 (13); 55 (20); 43 (44); 41 (18).

Major Trans-Isomers:
$^1$H-NMR (200 MHz, CDCl$_3$, selected data): δ (ppm) 3.32-3.52 (m, 1H); 3.61 (ddd, J=10.2 Hz, J=6.1 Hz, J=4.0 Hz, 1H).

$^{13}$C-NMR (50 MHz, CDCl$_3$, selected data): δ (ppm) 47.47 & 47.96; 69.34 & 69.58; 72.61 & 72.86; 100.19 & 100.26.

MS [e/m (%)]: 226 (M+, <1); 211 (92); 169 (88); 127 (15); 109 (100); 101 (53); 85 (44); 81 (14); 67 (61); 57 (26); 55 (40); 43 (86); 41 (34).

Example 31

Preparation of 4-methylhexahydro-4H-spiro[benzo[d][1,3]dioxine-2,1'-cyclopentane] (Iaj)

Compound Iaj is obtained as colourless oil in 16% yield, according to Example 23, from diol Va (40.57 g, 0.28 mol, obtained in Example 14), cyclopentanone (28.26 g, 0.34 mol) and cyclohexane (110 ml). It consists in a mixture of 2 isomers (97%) as cis/trans enantiomers in a 57:43 ratio.

Bp: 64-68° C./0.57 torr

Olfactory profile: Peanut, animal, clean.

Major Cis-Isomers:
$^1$H-NMR (200 MHz, CDCl$_3$): δ (ppm) 1.06 (d, J=6.6 Hz); 1.05-1.5 (m, 4H); 1.50-2.0 (m, 9H); 3.83-3.97 (m, 2H).

$^{13}$C-NMR (50 MHz, CDCl$_3$): δ (ppm) 18.12; 20.31; 22.61; 24.61; 24.64; 25.15; 31.49; 31.81; 39.40; 40.46; 69.49; 69.75; 110.36.

MS [e/m (%)]: 210 (M+, 9); 181 (48); 109 (100); 85 (32); 81 (11); 67 (61); 56 (17); 55 (63); 43 (13); 41 (25); 39 (11).

Major Trans-Isomers:
$^1$H-NMR (200 MHz, CDCl$_3$, selected data): δ (ppm) 0.70-0.95 (m, 1H); 1.12 (d, J=6.0 Hz, 3H); 3.34 (dt, J=10.2 Hz, J=3.8 Hz, 1H); 3.52 (qd, J=9.8 Hz, J=6.1 Hz, 1H).

$^{13}$C-NMR (50 MHz, CDCl$_3$): δ (ppm) 18.53; 18.91; 22.53; 24.48; 25.40; 25.86; 31.65; 32.0; 40.55; 47.75; 71.41; 74.80; 110.25.

MS [e/m (%)]: 210 (M+, 8); 182 (16); 181 (100); 109 (67); 85 (32); 81 (10); 67 (52); 56 (21); 55 (77); 43 (13); 41 (27); 39 (12).

Example 32

Preparation of 2-(2,4-dimethylcyclohex-3-enyl)-4-methylhexahydro-4H-benzo[d][1,3]dioxine (Iak)

Compound Iak is obtained as colourless oil in 28% yield, according to Example 23, from diol Va (40 g, 0.278 mol, obtained in Example 14), 2,4-dimethylcyclohex-3-enecarbaldehyde (Triplal™, 46 g, 0.333 mol) and cyclohexane (140 ml). It consists in a mixture of isomers, with 4 main isomers (85%) in a 42:31:16:11 ratio (cis/trans ratio: 58:42).

Bp: 105° C./0.4 torr

Olfactory profile: floral, green, a bit animalic.

Major Cis-Isomers:
$^1$H-NMR (200 MHz, CDCl$_3$): δ (ppm) 0.86 (d, J=6.8 Hz); 1.05-1.55 (m, 13H); 1.55-2.0 (m, 7H); 1.63 (s, 3H); 2.0-2.3 (m, 1H); 3.65-3.85 (m, 2H); 4.32-4.45 (m, 1H); 5.15 (br s, 1H).

$^{13}$C-NMR (50 MHz, CDCl$_3$, selected data): δ (ppm) 101.80 & 101.84; 127.56; 132.65.

MS [e/m (%)]: 264 (M+, 5); 249 (7); 155 (11); 138 (25); 137 (21); 127 (24); 123 (28); 120 (42); 110 (14); 109 (100); 107 (32); 95 (14); 93 (13); 91 (12); 81 (17); 79 (15); 67 (52); 55 (20); 41 (17).

Major Trans-Isomers:
$^1$H-NMR (200 MHz, CDCl$_3$, selected data): δ (ppm) 1.0 (d, J=7.0 Hz, 3H); 2.32-2.48 (m, 1H); 3.10-3.30 (m, 1H); 3.30-3.45 (m, 1H); 4.60-4.70 (m, 1H); 5.33 (br s, 1H).

$^{13}$C-NMR (50 MHz, CDCl$_3$, selected data): δ (ppm) 103.63 & 103.55; 127.52; 132.95.

MS [e/m (%)]: 264 (M+, 7); 249 (11); 155 (30); 138 (18); 137 (22); 127 (19); 123 (22); 120 (32); 110 (13); 109 (100); 107 (31); 95 (13); 93 (13); 91 (12); 81 (16); 79 (13); 67 (46); 55 (23); 41 (19).

Minor Cis-Isomers:
$^1$H-NMR (200 MHz, CDCl$_3$, selected data): δ (ppm) 3.65-3.85 (m, 2H); 4.60-4.70 (m, 1H); 5.33 (br s, 1H).

$^{13}$C-NMR (50 MHz, CDCl$_3$, selected data): δ (ppm) 102.02 & 102.12; 127.16; 133.05.

MS [e/m (%)]: 264 (M+, 11); 249 (21); 155 (15); 138 (20); 127 (15); 123 (10); 120 (15); 110 (10); 109 (100); 107 (18); 95 (13); 81 (15); 79 (12); 67 (44); 55 (16); 41 (13).

Minor Trans-Isomers:
$^1$H-NMR (200 MHz, CDCl$_3$, selected data): δ (ppm) 3.95-4.15 (m, 2H); 4.85-4.97 (m, 1H); 5.15 (br s, 1H).

$^{13}$C-NMR (50 MHz, CDCl$_3$, selected data): δ (ppm) 103.38; 127.35.

MS [e/m (%)]: 264 (M+, 15); 249 (41); 181 (11); 155 (50); 127 (16); 123 (12); 120 (14); 110 (10); 109 (100); 107 (16); 95 (12); 93 (10); 81 (16); 79 (12); 67 (43); 55 (19); 41 (16).

Example 33

Preparation of 4-methyl-4-a,5,6,7,8,8a-hexahydro-4H-spiro[benzo[d][1,3]dioxine-2,1'-cyclohex[2]ene] (Ial)

Compound Ial is obtained as colourless oil, according to Example 23, from diol Va (40 g, 0.278 mol, obtained in Example 14) and cyclohexenone. It consists in a mixture of isomers in a 25:31:20:24 ratio.

1st Isomers:
MS [e/m (%)]: 222 (M+, 15); 168 (97); 109 (100); 97 (12); 81 (13); 79 (16); 77 (12); 68 (22); 67 (55); 55 (24); 54 (24); 43 (10); 41 (26); 39 (19).

2nd Isomers:
MS [e/m (%)]: 222 (M+, 44); 168 (12); 109 (100); 97 (14); 96 (47); 81 (28); 79 (18); 68 (18); 67 (59); 55 (15); 54 (22); 53 (11); 43 (13); 41 (25); 39 (17).

3rd Isomers
MS [e/m (%)]: 222 (M+, 14); 168 (100); 109 (29); 97 (11); 81 (13); 79 (10); 68 (10); 67 (31); 55 (11); 54 (14).

4th Isomers:
MS [e/m (%)]; 222 (M+, 100); 207 (13); 168 (53); 114 (14); 109 (70); 97 (16); 96 (81); 95 (14); 81 (57); 79 (24); 77 (12); 68 (18); 67 (64); 55 (37); 54 (27); 53 (18); 43 (18); 41 (39); 39 (23).

Example 34

Preparation of
4-ethyl-2-isopropyl-hexahydro-benzo[1,3]dioxine
(Ibg)

Compound Ibg is obtained as colourless oil in 65% yield, according to Example 23, from diol Vb (35.65 g, 0.23 mol, obtained in Example 15), isobutyraldehyde (32.45 g, 0.45 mol) and cyclohexane (100 mL). It consists in a mixture of 6 isomers with 3 major isomers (85%) in a 63:20:17 ratio. The major enantiomers have the cis configuration.

Bp: 98° C./6.8 torr

Olfactory profile: herbaceous, camomile

1st Major Isomers (Cis-Isomers):
$^1$H-NMR (200 MHz, CDCl$_3$): δ (ppm) 0.85-1.00 (m, 3H); 0.94 (d, 3H, J=6.8 Hz); 0.95 (d, 3H, J=6.8 Hz); 1.01-1.82 (m, 10H); 1.83-1.75 (m, 2H); 3.41 (ddd, 1H, J=2.0 Hz, J=6.9 Hz, J=8.0 Hz); 3.72 (m, 1H); 4.30 (d, 1H, J=4.4 Hz).

$^{13}$C-NMR (50 MHz, CDCl$_3$): δ (ppm) 9.8; 16.7; 17.1; 19.6; 20.3; 24.7; 25.4; 31.9; 32.8; 37.9; 75.0; 81.2; 105.0.

MS [e/m (%)]: 211 (M$^+$, 6); 169 (51); 141 (3); 131 (18); 111 (5); 123 (100); 93 (11); 82 (77); 81 (59); 73 (28); 67 (64); 55 (21); 41 (24).

2nd Major Isomers:
$^{13}$C-NMR (50 MHz, CDCl$_3$, selected data): δ (ppm) 9.4; 25.4; 31.8; 32.8; 45.4; 80.5; 81.7; 105.5.

MS [e/m (%)]: idem 1st major isomer.

3rd Major Isomers:
$^1$H-NMR (200 MHz, CDCl$_3$, selected data): δ (ppm) 0.85-1.00 (m, 3H); 0.90 (d, 3H, J=6.8 Hz); 0.91 (d, 3H, J=6.8 Hz); 1.01-1.82 (m, 10H); 1.83-1.98 (m, 2H); 3.42 (m, 1H); 3.70 (ddd, 1H, J=3.9 Hz, J=5.5 Hz, J=11.9 Hz); 4.38 (d, 1H, J=5.6 Hz).

$^{13}$C-NMR (50 MHz, CDCl$_3$): δ (ppm) 9.9; 16.9; 17.5; 18.5; 24.5; 25.7; 26.4; 32.2; 32.7; 43.9; 74.8; 76.4; 97.9.

MS [e/m (%)]: 211 (M$^+$, 6); 169 (75); 141 (5); 123 (100); 111 (38); 93 (21); 82 (17); 81 (66); 73 (11); 67 (46); 55 (22); 41 (20).

1st Minor Isomers
$^{13}$C-NMR (50 MHz, CDCl$_3$, selected data): δ (ppm) 44.2; 74.9; 79.6; 97.6.

MS [e/m (%)]: idem 3rd major isomer.

Example 35

Preparation of
2-methyl-4-phenyl-hexahydro-benzo[1,3]dioxine
(Ica)

Compound Ica is obtained as white crystals in 25% yield, according to Example 23, from diol Vc (24.75 g, 0.12 mol, obtained in Example 16), acetaldehyde (17.29 g, 0.24 mol) and cyclohexane (50 mL). It consists in a mixture of 3 isomers with 1 major enantiomers (84%), as cis-isomers.

Bp: 88° C./0.3 torr

Mp: 57.4° C.

Olfactory profile: Spicy, exotic fruits

Major Cis-Isomers:
$^1$H-NMR (200 MHz, CDCl$_3$): δ (ppm) 0.85-1.20 (m, 2H); 1.21-1.51 (m, 2H); 1.47 (d, 3H, J=5.1 Hz); 1.52-1.72 (m, 4H); 1.98 (m, 1H); 4.02 (m, 1H); 4.80 (m, 1H); 4.94 (q, 1H, J=5.1 Hz); 7.29 (m, 5H).

$^{13}$C-NMR (50 MHz, CDCl$_3$): δ (ppm) 20.1; 20.6; 21.3; 25.4; 31.9; 40.4; 75.4; 81.2; 99.3; 125.5; 126.9; 128.1; 140.4.

MS [e/m (%)]: 189 (1); 188 (1); 171 (1); 151 (15); 129 (4); 117 (6); 107 (100); 91 (16); 82 (41); 67 (52); 54 (16); 41 (8); 39 (6).

1st Minor Isomers:
$^1$H-NMR (200 MHz, CDCl$_3$, selected data): δ (ppm) 1.36 (d, 3H, J=5.0 Hz); 3.90 (m, 1H).

$^{13}$C-NMR (50 MHz, CDCl$_3$, selected data): δ (ppm) 31.7; 47.0; 81.1; 84.3; 93.2; 127.3; 128.3.

2nd Minor Isomers:
$^1$H-NMR (200 MHz, CDCl$_3$, selected data): δ (ppm) 1.42 (d, 3H, J=5.1 Hz); 3.42 (dt, 1H, J=4.1 Hz, J=10.5 Hz); 4.23 (d, 1H, J=9.8 Hz); 4.97 (q, 1H, J=5.1 Hz).

Example 36

Preparation of 4-isobutyl-2-methylhexahydro-4H-benzo[d][1,3]dioxine (Ida)

Compound Ida is obtained as a colourless oil in 50% yield, according to Example 23, from diol Vd (24 g, 0.13 mol, obtained in Example 17), acetaldehyde (11.3 g, 0.26 mol) and cyclohexane (100 mL). It consists in a mixture of 6 isomers with 2 major isomers (75%) as cis/trans enantiomers in a 60:40 ratio.

Bp: 60° C./0.5 torr

Olfactory profile: Leathery, cresol.

Major Cis-Isomers:
$^1$H-NMR (200 MHz, CDCl$_3$): δ (ppm) 0.88 (d, J=6.6 Hz, 3H); 0.89 (d, J=6.6 Hz, 3H); 1.05-1.37 (m, 4H); 1.33 (d, J=5.1 Hz, 3H); 1.37-1.55 (m, 3H); 1.55-1.80 (m, 3H); 1.80-2.20 (m, 2H); 3.58-3.71 (m, 1H); 3.74-3.80 (m, 1H); 4.72 (q, J=5.09 Hz, 1H).

$^{13}$C-NMR (50 MHz, CDCl$_3$): δ (ppm) 19.84; 20.56; 21.21; 22.63; 22.94; 24.0; 25.33; 31.81; 38.16; 40.74; 75.43; 77.94; 98.89.

MS [e/m (%)]: 212 (M+, <0); 211 (2); 197 (1); 151 (3); 150 (3); 131 (14); 111 (4); 95 (13); 87 (16); (100); 69 (17); 67 (52); 55 (16); 43 (21); 41 (24).

Major Trans-Isomers:
$^1$H-NMR (200 MHz, CDCl$_3$, selected data): δ (ppm) 3.15-3.36 (m, 1H); 3.58-3.71 (m, 1H); 4.95 (m, 1H).

$^{13}$C-NMR (50 MHz, CDCl$_3$, selected data): δ (ppm) 25.72 & 25.79; 32.34 & 34.55; 43.67 & 45.93; 73.48 & 74.71; 78.85 & 80.69; 91.19 & 91.73.

MS [e/m (%)]: 212 (M+, <0); 211 (4); 197 (13); 155 (29); 151 (8); 131 (17); 111 (65); 95 (39); 93 (33); 87 (33); 83 (27); 82 (100); 81 (29); 79 (19); 69 (40); 67 (81); 57 (15); 55 (37); 54 (21); 45 (20); 43 (45); 41 (51); 39 (17).

1st Minor Isomers:
$^1$H-NMR (200 MHz, CDCl$_3$, selected data): δ (ppm) 3.42-3.60 (m, 1H); 3.96-4.05 (m, 1H); 4.76 (q, J=10.2 Hz, 1H)
$^{13}$C-NMR (50 MHz, CDCl$_3$, selected data): δ (ppm) 25.38; 31.61; 38.07; 98.56.
MS [e/m (%)]: 212 (M+, <0); 211 (3); 197 (27); 155 (26); 151 (10); 131 (7); 111 (100); 95 (53); 93 (45); 83 (18); 82 (61); 81 (31); 79 (17); 69 (40); 67 (72); 55 (36); 54 (18); 45 (15); 43 (40); 41 (46); 39 (15).

2nd Minor Isomers:
$^1$H-NMR (200 MHz, CDCl$_3$, selected data): δ (ppm) 5.07 (q, J=9.8 Hz, 1H).
MS [e/m (%)]: 212 (M+, <0); 211 (2); 197 (19); 151 (9); 150 (6); 131 (9); 111 (13); 95 (33); 87 (18); 83 (19); 82 (100); 81 (27); 79 (15); 69 (41); 67 (71); 57 (13); 55 (29); 54 (18); 45 (14); 43 (30); 41 (37); 39 (11).

Example 37

Preparation of 6-tert-butyl-2,4-dimethyl-hexahydro-benzo[1,3]dioxine (I'aa)

Compound I'aa is obtained as a yellow oil in 26% yield, according to Example 23, from diol V'a (48.74 g, 0.24 mol, obtained in Example 18), acetaldehyde (35.23 g, 0.49 mol) and cyclohexane (100 mL). It consists in a mixture of 6 isomers with 3 major isomers (65%) in a 42:29:29 ratio.
Bp: 58° C./0.3 torr
Olfactory profile: Sulfur, fatty.

1st Major Isomers (Cis-Isomers):
$^1$H-NMR (200 MHz, CDCl$_3$): δ (ppm) 0.86 (s, 9H); 0.90-1.92 (m, 7H); 1.16 (d, 3H, J=6.6 Hz); 1.33 (d, 3H, J=5.1 Hz); 1.99 (m, 1H); 3.73 (m, 1H); 3.83 (m, 1H); 4.74 (q, 1H, J=5.1 Hz).
$^{13}$C-NMR (50 MHz, CDCl$_3$): δ (ppm) 17.9; 21.2; 21.5; 25.6; 27.6; 32.6; 36.0; 39.8; 47.1; 74.9; 75.5; 98.7.
MS [e/m (%)]: 225, (M$^+$, 10); 211 (40); 165 (21); 149 (8); 138 (66); 125 (5); 109 (61); 108 (14); 95 (37); 83 (25); 82 (35); 81 (32); 80 (47); 79 (23); 67 (25); 57 (100); 55 (25); 43 (26); 41 (28).

2nd Major Isomers:
$^1$H-NMR (200 MHz, CDCl$_3$, selected data): δ (ppm) 0.85 (s, 9H); 4.68 (q, 1H, J=5.1 Hz).
$^{13}$C-NMR (50 MHz, CDCl$_3$, selected data): δ (ppm) 20.2; 29.4; 36.0.
MS [e/m (%)]: 225 (M$^+$, 2); 211 (2); 165 (5); 149 (10); 138 (21); 136 (100); 125 (20); 109 (24); 108 (11); 95 (18); 83 (19); 82 (29); 81 (29); 80 (38); 79 (22); 67 (21); 57 (74); 55 (21); 43 (22); 41 (24).

3rd Major Isomers:
$^1$H-NMR (200 MHz, CDCl$_3$): δ (ppm) 0.84 (s, 9H); 0.90-1.85 (m, 7H); 1.19 (d, 3H, J=6.3 Hz); 1.32 (d, 3H, J=5.1 Hz); 1.96 (m, 1H); 3.15 (ddd, 1H, J=4.1 Hz, J=9.8 Hz, J=11.2 Hz); 3.38 (dt, 1H, J=6.3 Hz, J=9.7 Hz); 4.78 (q, 1H, J=5.1 Hz).
$^{13}$C-NMR (50 MHz, CDCl$_3$, selected data): δ (ppm) 18.6; 21.2; 25.3; 26.5; 27.8; 31.6; 32.3; 46.7; 47.0; 77.1; 80.6; 98.4.
MS [e/m (%)]: idem 1st major isomers.

1st Minor Isomers:
$^1$H-NMR (200 MHz, CDCl$_3$, selected data): δ (ppm) 0.83 (s, 9H); 1.24 (d, 1H, J=7.0 Hz); 1.26 (d, 3H, J=5.1 Hz); 1.96 (m, 1H); 3.47 (dt, 1H, J=4.4 Hz, J=10.7 Hz); 4.07 (dq, 1H, J=7.0 Hz, J=12.8 Hz); 5.03 (q, 1H, J=5.1 Hz).
$^{13}$C-NMR (50 MHz, CDCl$_3$): δ (ppm) 13.0; 21.3; 25.3; 27.4; 27.5; 32.1; 32.2; 43.2; 47.5; 72.0; 74.2; 91.1.
MS [e/m (%)]: idem 1st major isomers.

2nd Minor Isomers:
$^1$H-NMR (200 MHz, CDCl$_3$, selected data): δ (ppm) 0.83 (s, 9H); 3.16 (m, 1H); 3.44 (m, 1H); 4.69 (q, 1H, J=5.1 Hz).
$^{13}$C-NMR (50 MHz, CDCl$_3$, selected data): δ (ppm) 18.0; 20.2; 25.6; 27.6; 32.0; 41.1; 47.1; 75.2; 75.7; 98.6.
MS [e/m (%)]: 211 (85); 165 (24); 149 (8); 138 (19); 125 (9); 109 (72); 108 (27); 95 (40); 83 (34); 82 (32); 81 (28); 80 (30); 79 (24); 67 (25); 57 (100); 55 (29); 43 (26); 41 (27).

Example 38

Preparation of 6-tert-butyl-4-ethyl-2-isopropyl-hexahydro-benzo[1,3]dioxine (I'bg)

Compound I'bg is obtained as a pale yellow oil in 21% yield, according to Example 23, from diol V' b (17.83 g, 0.08 mol, obtained in Example 19), isobutyraldehyde (7.19 g, 0.1 mol) and cyclohexane (40 mL). It consists in a mixture of 5 isomers with 2 major isomers (76%) as cis/trans enantiomers in a 63:37 ratio.
Bp: 88° C./0.7 torr
Olfactory profile: herbaceous, camomile, woody.

Major Cis-Isomers:
$^1$H-NMR (200 MHz, CDCl$_3$): δ (ppm) 0.84 (s, 9H); 0.87-1.00 (m, 3H); 0.92 (d, 6H, J=7.0 Hz); 1.01-1.70 (m, 9H); 1.77 (m, 1H); 1.19 (m, 1H); 3.42 (ddd, 1H, J=1.6 Hz; J=6.1 Hz, J=7.7 Hz); 3.64 (m, 1H); 4.28 (d, 1H, J=4.4 Hz).
$^{13}$C-NMR (50 MHz, CDCl$_3$): δ (ppm) 9.9; 16.7; 17.1; 20.4; 21.4; 24.7; 27.5; 32.1; 32.5; 32.8; 38.6; 47.0; 74.5; 81.2; 104.9.
MS [e/m (%)]: 267 (M$^+$, 6); 225 (62); 179 (53); 163 (4); 138 (33); 136 (1); 123 (63); 109 (45); 95 (27); 83 (19); 82 (28); 81 (30); 80 (47); 79 (19); 67 (22); 57 (100); 55 (18); 43 (18); 41 (27).

Major Trans-Isomers:
$^1$H-NMR (200 MHz, CDCl$_3$, selected data): δ (ppm) 0.85 (s, 9H); 0.91 (d, 6H, J=8.7 Hz); 3.42 (m, 1H); 3.75 (m, 1H); 4.22 (d, 1H, J=4.5 Hz).
$^{13}$C-NMR (50 MHz, CDCl$_3$): δ (ppm) 9.9; 16.8; 17.1; 19.0; 24.8; 28.0; 29.5; 32.4; 32.7; 33.3; 47.0; 75.4; 81.0; 104.8.
MS [e/m (%)]: 267 (M$^+$, 3); 225 (23); 179 (49); 163 (7); 138 (25); 136 (49); 123 (66); 109 (42); 95 (27); 83 (20); 82 (27); 81 (29); 80 (42); 79 (22); 67 (23); 57 (100); 55 (20); 43 (19); 41 (29).

1st Minor Isomers:
$^1$H-NMR (200 MHz, CDCl$_3$, selected data): δ (ppm) 0.83 (s, 9H); 0.93 (d, 6H, J=6.8 Hz); 3.09 (m, 2H); 4.23 (d, 1H, J=5.6 Hz).
$^{13}$C-NMR (50 MHz, CDCl$_3$, selected data): δ (ppm) 9.5; 17.2; 17.6; 25.1; 25.2; 26.3; 27.6; 31.7; 32.8; 44.9; 47.1; 80.6; 81.9; 105.4.
MS [e/m (%)]: idem major cis isomers.

2nd Minor Isomers:
$^1$H-NMR (200 MHz, CDCl$_3$, selected data): δ (ppm) 4.50 (d, 1H, J=4.2 Hz).
MS [e/m (%)]: idem major cis isomers.

3rd Minor Isomers:
$^1$H-NMR (200 MHz, CDCl$_3$, selected data): δ (ppm) 4.41 (d, 1H, J=5.6 Hz).
MS [e/m (%)]: idem major cis isomers.

Example 39

Preparation of 6-tert-butyl-2-methyl-4-phenyl-hexahydro-benzo[1,3]dioxine (I'ca)

Compound I'ca is obtained as white crystals in 21% yield, according to Example 23, from diol V'c (11.55 g, 0.04 mol, obtained in Example 20), acetaldehyde (3.87 g, 0.09 mol) and cyclohexane (20 mL). It consists in a mixture of 3 isomers with 2 major isomers (77%) as cis isomers in a 56:44 ratio. The crude product was purified by column chromatography on $SiO_2$ (AcOEt/Hexane (5:95)) The cis isomers were obtained as white crystals, whereas the minor trans isomer was obtained as a colourless oil.

Olfactory profile: green, chemicals.

Major Cis-Isomers:
$^1$H-NMR (200 MHz, $CDCl_3$): δ (ppm) 0.73 (s, 9H); 0.80-1.80 (m, 7H); 1.46 (d, 3H, J=5.1 Hz); 2.08 (m, 1H); 3.96 (m, 1H); 4.84 (m, 1H); 4.93 (m, 1H); 7.29 (m, 5H).

$^{13}$C-NMR (50 MHz, $CDCl_3$): δ (ppm) 20.7; 21.2; 21.4; 27.4; 32.1; 32.5; 40.8; 47.1; 74.9; 81.1; 99.1; 125.3; 126.8; 127.9; 140.0.

MS [e/m (%)]:287 ($M^+$, 1); 229 (2); 151 (27); 138 (20); 107 (100); 80 (24); 77 (7); 57 (30); 51 (1); 39 (2).

Minor Cis-Isomers:
$^1$H-NMR (200 MHz, $CDCl_3$, selected data): δ (ppm) 0.71 (s, 9H); 1.45 (d, 3H, J=5.1 Hz); 4.08 (m, 1H).

$^{13}$C-NMR (50 MHz, $CDCl_3$): δ (ppm) 19.1; 20; 21.2; 27.9; 29.3; 33.4; 35.6; 41.1; 75.4; 80.3; 98.7; 125.1; 126.7; 127.9; 140.3.

MS [e/m (%)]: idem cis-isomers.

Minor Trans-Isomers:
$^1$H-NMR (200 MHz, $CDCl_3$): δ (ppm) 0.74 (s, 9H); 0.80-1.75 (m, 6H); 1.42 (d, 3H, J=5.1 Hz); 1.76-1.95 (m, 1H); 2.03 (m, 1H); 3.37 (ddd, 1H, J=4.2 Hz, J=9.7 Hz, J=11.2 Hz); 4.24 (d, 1H, J=9.9 Hz); 4.98 (q, 1H, J=5.1 Hz); 7.31 (m, 5H).

$^{13}$C-NMR (50 MHz, $CDCl_3$): δ (ppm) 21.3; 25.4; 26.4; 27.5; 31.7; 32.3; 46.3; 46.8; 80.3; 84.4; 99.1; 127.3; 128.0; 128.3; 139.4.

MS [e/m (%)]: idem major cis isomers.

Example 40

Preparation of 2,4,6,6-tetra-methyl-hexahydro-benzo[1,3]dioxine (I"aa)

Compound I"aa is obtained as a colourless oil in 58% yield, according to Example 23, from diol V"a (74.08 g, 0.43 mol, obtained in Example 21), acetaldehyde (61.95 g, 0.86 mol) and cyclohexane (180 mL). It consists in a mixture of 4 isomers with 2 major isomers (75%) as cis/trans enantiomers in a 55:45 ratio.

Bp: 52° C./1.1 torr

Olfactory profile: Aromatic, woody, powerful.

Major Cis-Isomers:
$^1$H-NMR (200 MHz, $CDCl_3$): δ (ppm) 0.86 (s, 3H); 0.94 (s, 3H); 0.95-1.65 (m, 6H); 1.11 (d, 3H, J=6.6 Hz); 1.32 (d, 3H, J=5.1 Hz); 1.72 (m, 1H); 3.72 (m, 1H); 3.82 (dq, 1H, J=2.4 Hz, J=6.6 Hz); 4.72 (q, 1H, J=5.1 Hz).

$^{13}$C-NMR (50 MHz, $CDCl_3$): δ (ppm) 17.8; 21.2; 24.2; 27.6; 29.9; 32.1; 33.0; 33.2; 35.4; 74.7; 75.3; 98.7.

MS [e/m (%)]: 197 ($M^+$, 4); 183 (8); 155 (2); 137 (31); 110 (100); 95 (67); 89 (22); 81 (63); 69 (11); 55 (16); 43 (20).

Major Trans-Isomers:
$^1$H-NMR (200 MHz, $CDCl_3$, selected data): δ (ppm) 0.91 (s, 3H); 0.94 (s, 3H); 1.16 (d, 3H, J=6.3 Hz); 1.33 (d, 3H, J=5.1 Hz); 3.15 (ddd, 1H, J=4.6 Hz, J=9.7 Hz, J=10.9 Hz); 3.35 (dq, 1H, J=6.3 Hz, J=9.3 Hz); 4.78 (q, 1H, J=5.1 Hz).

$^{13}$C-NMR (50 MHz, $CDCl_3$): δ (ppm) 18.5; 21.2; 25.2; 27.7; 30.7; 32.7; 37.3; 38.9; 42.6; 77.3; 81.1; 98.5.

MS [e/m (%)]: 197 ($M^+$, 15); 183 (95); 155 (3); 137 (57); 110 (95); 95 (97); 81 (100); 69 (21); 55 (28); 43 (33); 41 (23).

1$^{st}$ Minor Isomers:
MS [e/m (%)]:197 ($M^+$, 11); 183 (100); 155 (8); 137 (68); 110 (42); 95 (68); 81 (77); 69 (19); 55 (24); 43 (28); 41 (19).

Example 41

Preparation of 4,6,6-trimethyl-2-((E)-propenyl)-hexahydro-benzo[1,3]dioxine (I"ac)

Compound I"ac is obtained as a yellow oil in 56% yield, according to Example 23, from diol V"a (31.01 g, 0.18 mol, obtained in Example 21), crotonaldehyde (14.72 g, 0.21 mol) and cyclohexane (80 mL). It consists in a mixture of 8 isomers with 2 major isomers (76%) as cis/trans enantiomers in a 55:45 ratio.

Bp: 80° C./0.8 torr

Olfactory profile: herbal, minty, fruity

Major Cis-Isomers:
$^1$H-NMR (200 MHz, $CDCl_3$): δ (ppm) 0.96 (s, 6H); 1.00-1.65 (m, 6H); 1.19 (d, 3H, J=9.0 Hz); 1.17-1.85 (m, 1H); 1.71 (d, 3H, J=1.3 Hz); 3.23 (ddd, 1H, J=4.6 Hz, J=10.0 Hz, J=10.7 Hz); 3.44 (dq, 1H, J=6.1 Hz, J=9.0 Hz); 5.04 (d, 1H, J=5.6 Hz); 5.60 (m, 1H); 5.93 (m, 1H).

$^{13}$C-NMR (50 MHz, $CDCl_3$): δ (ppm) 17.7; 25.2; 27.6; 30.7; 32.0; 32.7; 38.9; 42.7; 74.8; 75.4; 100.7; 128.3; 130.7.

MS [e/m (%)]: 223 ($M^+$, 16); 210 (8); 209 (60); 183 (4); 137(44); 99 (14); 95 (59); 81 (80); 71 (100); 69 (42); 55 (32); 43 (22); 41 (30).

Major Trans-Isomers:
$^1$H-NMR (200 MHz, $CDCl_3$, selected data): δ (ppm) 0.88 (s, 3H); 0.93 (s, 3H); 1.16 (d, 3H, J=8.9 Hz); 1.74 (d, 3H, J=1.4 Hz); 3.81 (m, 1H); 3.89 (m, 1H); 4.97 (d, 1H, J=6.0 Hz).

$^{13}$C-NMR (50 MHz, $CDCl_3$): δ (ppm) 17.8; 24.2; 27.7; 29.8; 32.9; 33.1; 35.5; 37.3; 77.4; 81.1; 101.2; 128.6; 130.8.

MS [e/m (%)]: idem cis-isomers.

1$^{st}$ Minor Isomers:
$^{13}$C-NMR (50 MHz, $CDCl_3$, selected data): δ (ppm) 96.9; 127.7; 129.8.

MS [e/m (%)]: idem cis-isomers.

2$^{nd}$ Minor Isomers:
$^{13}$C-NMR (50 MHz, $CDCl_3$, selected data): δ (ppm) 97.1; 127.9; 129.9.

MS [e/m (%)]: idem cis-isomers.

Other Minor Isomers:
MS [e/m (%)]: 210 (12); 209 (92); 137 (100); 127 (9); 99 (1); 95 (15); 81 (12); 71 (4); 69 (7); 55 (19); 43 (8); 41 (8).

Example 42

Preparation of 4-ethyl-2-isopropyl-6,6-dimethyl-hexahydro-benzo[1,3]dioxine (I"bg)

Compound I"bg is obtained as a colourless oil in 31% yield, according to Example 23, from diol V"b (29.81 g, 0.16 mol, obtained in Example 22), isobutyraldehyde (23.05 g, 0.32 mol) and cyclohexane (70 mL). It consists in a mixture of 4 isomers with 2 major isomers (74%) as cis/trans enantiomers in a 60:40 ratio.

Bp: 106° C./5.9 torr

Olfactory profile: herbaceous

Major Cis-Isomers:

$^1$H-NMR (200 MHz, CDCl$_3$): δ (ppm) 0.55-1.00 (m, 15H); 1.01-1.67 (m, 8H); 1.68-1.90 (m, 2H); 3.44 (ddd, 1H, J=4.0 Hz, J=7.4 Hz, J=10.0 Hz); 3.66 (m, 1H); 4.27 (d, 1H, J=4.6 Hz).

$^{13}$C-NMR (50 MHz, CDCl$_3$): δ (ppm) 9.8; 17.3; 24.2; 24.6; 27.8; 29.9; 32.4; 32.9; 33.3; 34.1; 37.3; 69.1; 80.9; 105.0.

MS [e/m (%)]: 239 (M$^+$, 4); 197 (34); 151 (100); 139 (1); 110 (70); 109 (25); 95 (69); 81 (45); 69 (17); 55 (15); 43 (18); 41 (21).

Major Trans-Isomers:

$^1$H-NMR (200 MHz, CDCl$_3$, selected data): δ (ppm) 3.10 (m, 1H); 3.44 (m, 1H); 4.41 (d, 1H, J=5.7 Hz).

$^{13}$C-NMR (50 MHz, CDCl$_3$): δ (ppm) 10.0; 18.5; 24.6; 28.3; 30.9; 33.2; 39.4; 74.5; 77.2; 97.7.

MS [e/m (%)]: 239 (M$^+$, 5); 197 (69); 151 (68); 139 (26); 110 (14); 109 (27); 95 (100); 81 (44); 69 (27); 55 (24); 43 (23); 41 (24).

1$^{st}$ Minor Isomers:

$^1$H-NMR (200 MHz, CDCl$_3$, selected data): δ (ppm) 4.24 (d, 1H, J=6.0 Hz).

$^{13}$C-NMR (50 MHz, CDCl$_3$, selected data): δ (ppm) 105.6.

MS [e/m (%)]: 239 (M$^+$, 5); 197 (54); 151 (41); 139 (3); 110 (48); 109 (17); 95 (100); 81 (53); 69 (20); 55 (19); 43 (18); 41 (21).

2$^{nd}$ Minor Isomers:

$^1$H-NMR (200 MHz, CDCl$_3$, selected data): δ (ppm) 4.48 (d, 1H, J=4.7 Hz).

$^{13}$C-NMR (50 MHz, CDCl$_3$, selected data): δ (ppm) 97.5.

MS [e/m (%)]: 239 (M$^+$, 4); 197 (65); 151 (100); 139 (22); 110 (12); 109 (26); 95 (63); 81 (29); 69 (24); 55 (20); 43 (20); 41 (19).

Example 43

Fragrance Composition Comprising the Compound Obtained in Example 28

A green woody fougere composition was prepared from the following ingredients:

| Ingredients | Composition A | Composition B |
|---|---|---|
| Adoxal ® 10% in DPG. | 3 | 3 |
| Allyl amyl glycolate | 15 | 15 |
| Basilic Indes ess. | 3 | 3 |
| Bergamote | 100 | 100 |
| Bouleau feuilles | 5 | 5 |
| Calone 1951 ® 10% in DPG | 10 | 10 |
| Cedramber ® | 60 | 60 |
| Cedre feuilles ess. | 5 | 5 |
| Cinnamique 10% in DPG | 5 | 5 |
| Citron | 50 | 50 |
| Citronellol pur | 10 | 10 |
| Corps lrg 0201 10% in DPG | 40 | 40 |
| Coumarine 10% in DPG | 150 | 150 |
| Dihydromyrcenol | 90 | 90 |
| Eugenol rect. VMF | 10 | 10 |
| Floralozone ® 10% in DPG | 15 | 15 |
| Folione ® 10% in DPG | 1 | 1 |
| *Geranium* chine ess. | 5 | 5 |
| Helional ® | 15 | 15 |
| cis-3-Hexenol 10% in DPG | 10 | 10 |
| Ionone beta | 15 | 15 |
| Lavandin grosso ess. | 10 | 10 |
| Linalol | 25 | 25 |
| Linalyle acetate | 50 | 50 |
| Mazarine ® | 5 | 5 |
| Melonal ® 10% in DPG | 5 | 5 |
| Methyl dihydrojasmonate | 50 | 50 |

-continued

| Ingredients | Composition A | Composition B |
|---|---|---|
| cis-6-Nonenol 1% in DPG | 5 | 5 |
| Octahydro tetramethyl acetonaphtone | 133 | 133 |
| Orcanox ® | 1 | 1 |
| Patchouly ess. | 15 | 15 |
| Quinoleine isobutyl 10% in DPG | 5 | 5 |
| Sandalore ® | 20 | 20 |
| Styrallyle acetate | 5 | 5 |
| Verdox ® 50% in DPG | 54 | 54 |
| 2-Ethyl-4-methylhexahydro-4H-benzo[d][1,3]dioxine (Example 28) | — | 10 |
| DPG | 100 | 90 |
| TOTAL | 1000 | 1000 |

Evaluated at usual dilution in alcohol, composition A was described as very aromatic, with a tarragon note and a cystemoss dry-down note whereas composition B (containing 2-ethyl-4-methylhexahydro-4H-benzo[d][1,3]dioxine) has a fresher note (hesperidic, grapefruit, with a slight sulphur undertone) and marine facets giving a more modern impact to the fragrance.

Evaluated at usual dilution in a shower gel base, compositions A and B show no real difference in the fragrance perception, however adding 2-ethyl-4-methylhexahydro-4H-benzo[d][1,3]dioxine to the composition brings more power to the note.

Example 44

Fragrance Composition Comprising the Compound Obtained in Example 28

A floral hesperidic watery composition was prepared from the following ingredients:

| Ingredients | Composition A | Composition B |
|---|---|---|
| Allyl Cyclohexylpropionate | 1 | 1 |
| Ambrettolide VMF | 10 | 10 |
| Benzyl Salicylate 50% in DPG | 30 | 30 |
| Bourgeonal ® | 3 | 3 |
| Calone 1951 ® 10% in DPG | 12 | 12 |
| Citron | 104 | 104 |
| Citronellyl acetate | 2 | 2 |
| Corps LRG 0201 10% in DPG | 10 | 10 |
| Methylpamplemousse | 10 | 10 |
| Cyclamen Aldehyde Extra ® | 1 | 1 |
| Cyclemone A ® 10% in DPG | 50 | 50 |
| Dihydromyrcenol | 10 | 10 |
| Ethyl Linalol | 25 | 25 |
| Floralozone ® | 1 | 1 |
| Florol ® | 35 | 35 |
| Gamma Decalactone 10% in DPG | 8 | 8 |
| Geraniol | 10 | 10 |
| Hexalon ® | 3 | 3 |
| cis-3-Hexenol 10% in DPG | 50 | 50 |
| cis-3-Hexenyl Acetate 10% in DPG | 3 | 3 |
| Hexylcinnamic aldehyde | 20 | 20 |
| Indol 10% in DPG | 1 | 1 |
| Ionone Beta | 10 | 10 |
| Lemarome ® | 2 | 2 |
| Liffarome ® 10% in DPG | 6 | 6 |
| Linalol | 35 | 35 |
| Linalyl Acetate | 60 | 60 |
| Melonal ® 10% in DPG | 4 | 4 |
| Methyl dihydrojasmonate | 142 | 142 |
| Octahydro tetramethyl acetonaphtone | 35 | 35 |
| Orange Bresil val. Ess. | 80 | 80 |
| Patchouly Ess. | 4 | 4 |
| Styrallyl acetate | 2 | 2 |
| Triplal ® 10% in DPG | 15 | 15 |

-continued

| Ingredients | Composition A | Composition B |
| --- | --- | --- |
| Vanilline 10% in DPG | 4 | 4 |
| Verdox ® 50% in DPG | 2 | 2 |
| DPG | 200 | 195 |
| 2-Ethyl-4-methylhexahydro-4H-benzo[d][1,3]dioxine (Example 28) | — | 5 |
| TOTAL | 800 | 800 |

These two compositions were used in a shower gel base and in alcohol at usual dilutions, known from the person of the art, and the samples containing the compound 2-ethyl-4-methylhexahydro-4H-benzo[d][1,3]dioxine showed a fresher lemon zest note.

In alcohol, composition B was also described as having green aciduous facets with a more floral indolic middle note, imparting a nicer and less "technique" impact to the fragrance.

Example 45

Fragrance Composition Comprising the Compound Obtained in Example 27

A wisteria accord was prepared from the following ingredients:

| Ingredients | Composition A | Composition B |
| --- | --- | --- |
| Ambrettolide | 20 | 20 |
| Anisic aldehyde | 20 | 20 |
| Benzyl acetate | 40 | 40 |
| Benzylsalicylate | 125 | 125 |
| Cinnamyl acetate | 50 | 50 |
| DPG | 10 | — |
| Geraniol | 200 | 200 |
| Heliotropine | 50 | 50 |
| Hydroxycitronellal | 120 | 120 |
| Isobutyl phenylacetate | 50 | 50 |
| Jasmine Absopop ™ | 10 | 10 |
| Methyl phenylacetate | 5 | 5 |
| *Mimosa* Inde abs. | 20 | 20 |
| Oranger Absopop ™ | 10 | 10 |
| Phenylethyl alcohol | 60 | 60 |
| Terpineol | 100 | 100 |
| Ylang-Ylang ess. extra | 60 | 60 |
| 2-Benzyl-4-methyl-hexahydro-benzo[1,3]dioxine (Example 27) | — | 10 |
| TOTAL | 950 | 950 |

Adding 2-benzyl-4-methyl-hexahydro-benzo[1,3]dioxine to Composition A (Composition B) brings a more floral, honey-like and natural aspect to the wisteria accord, giving a rounder, sugary facet, with some lily-of-the-valley undertone.

Example 46

Fragrance Composition Containing the Derivative Obtained in Example 27

A rose accord was prepared from the following ingredients:

| Ingredients | Composition A | Composition B |
| --- | --- | --- |
| Aldehyde C11 lenique, 10% DPG | 7 | 7 |
| Bacdanol ® | 4 | 4 |
| Citronellol | 240 | 240 |
| Citronellyl acetate | 3 | 3 |
| DPG | 10 | — |
| Eugenol | 3 | 3 |
| Geraniol | 30 | 30 |
| Lilial ® | 15 | 15 |
| Methyl phenylacetate | 6 | 6 |
| Methylionantheme | 15 | 15 |
| Phenyl oxide | 6 | 6 |
| Phenylacetic aldehyde dimethyl acetal | 5 | 5 |
| Phenylethyl acetate | 6 | 6 |
| Phenylethyl alcohol | 420 | 420 |
| Rosafix ® | 15 | 15 |
| Triplal ® | 5 | 5 |
| 2-Benzyl-4-methyl-hexahydro-benzo[1,3]dioxine (Example 27) | — | 10 |
| TOTAL | 790 | 790 |

Adding 2-benzyl-4-methyl-hexahydro-benzo[1,3]dioxine to Composition A (Composition B) gives a more natural and green aspect to the rose accord and adds sweet, powdery facets.

Example 47

Fragrance Composition Comprising the Compound Obtained in Example 27

A mimosa accord was prepared from the following ingredients:

| Ingredients | Composition A | Composition B |
| --- | --- | --- |
| Anisic aldehyde | 130 | 130 |
| DPG | 485 | 475 |
| Heliotropine | 15 | 15 |
| Hexyl cinnamic aldehyde | 370 | 370 |
| 2-Benzyl-4-methyl-hexahydro-benzo[1,3]dioxine (Example 27) | — | 10 |
| TOTAL | 1000 | 1000 |

Adding 2-benzyl-4-methyl-hexahydro-benzo[1,3]dioxine to Composition A (Composition B) really impacts the fragrance to a nice mimosa note, with powdery and green aspects.

Example 48

Fragrance Composition Comprising the Compound Obtained in Example 27

A nenuphar accord was prepared from the following ingredients:

| Ingredients | Composition A | Composition B |
| --- | --- | --- |
| Benzyl acetate | 360 | 360 |
| Beta-Ionone | 28 | 28 |
| Canthoxal | 4 | 4 |
| Dihydromyrcenol | 90 | 90 |
| DPG | 10 | — |
| Ethyl phtalate | 52 | 52 |
| EThyl vanillin | 2 | 2 |
| Eugenol | 8 | 8 |

-continued

| Ingredients | Composition A | Composition B |
|---|---|---|
| Gamma-decalactone | 4 | 4 |
| Geraniol | 15 | 15 |
| Helional | 8 | 8 |
| Hexyl acetate | 10 | 10 |
| Hexyl cinnamic aldehyde | 20 | 20 |
| Indol | 2 | 2 |
| Lauric aldehyde | 2 | 2 |
| Linalol | 160 | 160 |
| Melonal | 2 | 2 |
| Methyl dihydro jasmonate | 120 | 120 |
| Musc T | 30 | 30 |
| Phenyl ethyl alcohol | 50 | 50 |
| Propyl gaiacol | 8 | 8 |
| Triplal | 1 | 1 |
| 2-Benzyl-4-methyl-hexahydro-benzo[1,3]dioxine (Example 27) | — | 10 |
| TOTAL | 790 | 790 |

Adding 2-benzyl-4-methyl-hexahydro-benzo[1,3]dioxine to Composition A (Composition B) gives a more natural and sweet water-lily note, with a slight jasminic facet.

The invention claimed is:
1. A compound of formula:

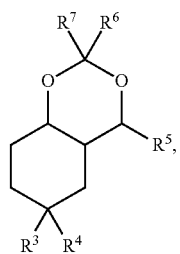

(I)

wherein:
$R^3$ and $R^4$ are independently a hydrogen atom, a C1-C6 alkyl group or a C2-C6 alkenyl group,
$R^5$ is selected from the group consisting of methyl, ethyl, i-butyl, t-butyl, n-pentyl, a C2-C6 alkenyl group and a $(CH_2)_{0-2}$-aryl group,
$R^6$ is a C1-C6 alkyl group, a C2-C6 alkenyl group, a $(CH_2)_{0-2}$-aryl group or a C5-C6 cycloalkyl or cycloalkenyl group, and
$R^7$ is a hydrogen atom, a C1-C6 alkyl group or a C2-C6 alkenyl group;
or
$R^3$, $R^4$ and $R^5$ are as above defined, and
$R^6$ and $R^7$ together with the carbon atom to which they are attached form a C5-C6 cycloalkyl or cycloalkenyl group;
with the proviso that said compound is not:
2,2-dimethyl-4-ethylhexahydrobenzo[1,3]dioxine
2,2-dimethyl-4-n-penthylhexahydrobenzo[1,3]dioxine
2,2-dimethyl-4-phenylhexahydrobenzo[1,3]dioxine
2,4-dimethylhexahydrobenzo[1,3]dioxine
2,4-diphenylhexahydrobenzo[1,3]dioxine
4-ethyl-2-methylhexahydrobenzo[1,3]dioxine
4-methyl-2-phenylhexahydrobenzo[1,3]dioxine
2,2,4-trimethylhexahydrobenzo[1,3]dioxine.
2. The compound according to claim 1, wherein:
$R^3$ and $R^4$ are independently selected from the group consisting of a hydrogen atom, methyl, ethyl, i-propyl, i-butyl and t-butyl,
$R^5$ is selected from the group consisting of methyl, ethyl, i-butyl, t-butyl, n-pentyl, 1-propen-1-yl, allyl, vinyl and phenyl,
$R^6$ is selected from the group consisting of methyl, ethyl, n-propyl, i-propyl, n-butyl, i-butyl, t-butyl, n-pentyl, 1-propen-1-yl, phenyl, benzyl and 2,4-dimethylcyclohexen-3-yl, and
$R^7$ is selected from the group consisting of a hydrogen atom, methyl, ethyl, n-propyl, i-propyl, n-butyl, i-butyl, t-butyl, n-pentyl and 1-propen-1-yl.
3. The compound according to claim 1, wherein:
$R^3$ and $R^4$ are hydrogen atoms,
$R^5$ is selected from the group consisting of methyl, ethyl, i-butyl and phenyl,
$R^6$ is selected from the group consisting of methyl, ethyl, i-propyl, phenyl, benzyl and 2,4-dimethylcyclohexen-3-yl, and
$R^7$ is selected from the group consisting of a hydrogen atom, methyl and n-butyl.
4. The compound according to claim 3, wherein:
$R^3$, $R^4$ and $R^7$ are hydrogen atoms, and
$R^5$ is methyl, and
$R^6$ is ethyl or benzyl.
5. The compound according to claim 1, wherein:
$R^3$ and $R^7$ are hydrogen atoms,
$R^4$ is t-butyl,
$R^5$ is methyl, ethyl or phenyl, and
$R^6$ is methyl or i-propyl.
6. The compound according to claim 1, wherein:
$R^3$ and $R^4$ are methyls,
$R^5$ is methyl or ethyl,
$R^6$ is selected from the group consisting of methyl, i-propyl and 1-propen-1-yl, and
$R^7$ is a hydrogen atom.
7. A fragrant composition comprising, as a fragrant agent, at least one compound of formula:

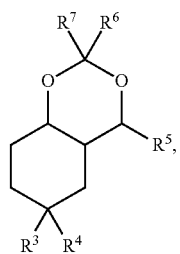

(I)

wherein:
$R^3$ and $R^4$ are independently a hydrogen atom, a C1-C6 alkyl group or a C2-C6 alkenyl group,
$R^5$ is a C1-C6 alkyl group, a C2-C6 alkenyl group or a $(CH_2)_{0-2}$-aryl group,
$R^6$ is a C1-C6 alkyl group, a C2-C6 alkenyl group, a $(CH_2)_{0-2}$-aryl group or a C5-C6 cycloalkyl or cycloalkenyl group, and
$R^7$ is a hydrogen atom, a C1-C6 alkyl group or a C2-C6 alkenyl group;
or
$R^3$, $R^4$ and $R^5$ are as above defined, and
$R^6$ and $R^7$ together with the carbon atom to which they are attached form a C5-C6 cycloalkyl or cycloalkenyl group.

8. The composition according to claim 7, selected from the group consisting of perfumed bases, concentrates, fragrances, perfumes and similar products.

9. The composition according to claim 7, as a masking agent of odours.

10. The composition according to claim 7, comprising, as a fragrant agent, at least one compound wherein:
$R^3$ and $R^4$ are independently selected from the group consisting of a hydrogen atom, methyl, ethyl, i-propyl, i-butyl and t-butyl,
$R^5$ is selected from the group consisting of methyl, ethyl, i-propyl, i-butyl, t-butyl, n-pentyl, 1-propen-1-yl, allyl, vinyl and phenyl,
$R^6$ is selected from the group consisting of methyl, ethyl, n-propyl, i-propyl, n-butyl, i-butyl, t-butyl, n-pentyl, 1-propen-1-yl, phenyl, benzyl and 2,4-dimethylcyclohexen-3-yl, and
$R^7$ is selected from the group consisting of a hydrogen atom, methyl, ethyl, n-propyl, i-propyl, n-butyl, i-butyl, t-butyl, n-pentyl and 1-propen-1-yl.

11. The composition according to claim 7, comprising, as a fragrant agent, at least one compound wherein:
$R^3$ and $R^4$ are hydrogen atoms,
$R^5$ is selected from the group consisting of methyl, ethyl, i-butyl and phenyl,
$R^6$ is selected from the group consisting of methyl, ethyl, i-propyl, phenyl, benzyl and 2,4-dimethylcyclohexen-3-yl, and
$R^7$ is selected from the group consisting of a hydrogen atom, methyl and n-butyl.

12. The composition according to claim 7, comprising, as a fragrant agent, at least one compound wherein:
$R^3$, $R^4$ and $R^7$ are hydrogen atoms, and
$R^5$ is methyl, and
$R^6$ is ethyl or benzyl.

13. The composition according to claim 7, comprising, as a fragrant agent, at least one compound wherein:
$R^3$ and $R^7$ are hydrogen atoms,
$R^4$ is t-butyl,
$R^5$ is methyl, ethyl or phenyl, and
$R^6$ is methyl or i-propyl.

14. The composition according to claim 7, comprising, as a fragrant agent, at least one compound wherein:
$R^3$ and $R^4$ are methyls,
$R^5$ is methyl or ethyl,
$R^6$ is selected from the group consisting of methyl, i-propyl and 1-propen-1-yl, and
$R^7$ is a hydrogen atom.

15. The composition according to claim 7, comprising, as a fragrant agent, at least one compound, selected in from the group consisting of:
2,4-dimethyl-hexahydro-benzo[1,3]dioxine
4-methyl-2-pentyl-hexahydro-benzo[1,3]dioxine
4-methyl-2-propenyl-hexahydro-benzo[1,3]dioxine
4-methyl-2-phenyl-hexahydro-benzo[1,3]dioxine
2-benzyl-4-methyl-hexahydro-benzo[1,3]dioxine
2-ethyl-4-methylhexahydro-4H-benzo[d][1,3]dioxine
2,2,4-trimethylhexahydro-4H-benzo[d][1,3]dioxine
2-butyl-2,4-dimethylhexahydro-4H-benzo[d][1,3]dioxine
4-methylhexahydro-4H-spiro[benzo[d][1,3]dioxine-2,1'-cyclopentane]
2-(2,4-dimethylcyclohex-3-enyl)-4-methylhexahydro-4H-benzo[d][1,3]dioxine
2-(2,4-dimethylcyclohex-3-enyl)-4-methylhexahydro-4H-benzo[d][1,3]dioxine
4-ethyl-2-isopropyl-hexahydro-benzo[1,3]dioxine
2-methyl-4-phenyl-hexahydro-benzo[1,3]dioxine
4-isobutyl-2-methylhexahydro-4H-benzo[d][1,3]dioxine
6-tert-butyl-2,4-dimethyl-hexahydro-benzo[1,3]dioxine
6-tert-butyl-4-ethyl-2-isopropyl-hexahydro-benzo[1,3]dioxine
6-tert-butyl-2-methyl-4-phenyl-hexahydro-benzo[1,3]dioxine
2,4,6,6-tetra-methyl-hexahydro-benzo[1,3]dioxine
4,6,6-trimethyl-2-((E)-propenyl)-hexahydro-benzo[1,3]dioxine
4-ethyl-2-isopropyl-6,6-dimethyl-hexahydro-benzo[1,3]dioxine.

* * * * *